United States Patent
Mullis et al.

(10) Patent No.: US 11,161,107 B2
(45) Date of Patent: Nov. 2, 2021

(54) DISPERSIVE PIPETTE EXTRACTION SYSTEM FOR PURIFICATION OF LARGE BIOMOLECULES

(71) Applicant: INTEGRATED MICRO-CHROMATOGRAPHY SYSTEMS, INC., Irmo, SC (US)

(72) Inventors: Brian Todd Mullis, Columbia, SC (US); Gary Horvath, Columbia, SC (US); Lim Andrew Lee, Columbia, SC (US); Sunil Hwang, Charlotte, NC (US); William Edward Brewer, Columbia, SC (US)

(73) Assignee: INTEGRATED MICRO-CHROMATOGRAPHY SYSTEMS, INC., Irmo, SC (US)

( * ) Notice: Subject to any disclaimer, the term of this patent is extended or adjusted under 35 U.S.C. 154(b) by 1020 days.

(21) Appl. No.: 15/605,393

(22) Filed: May 25, 2017

(65) Prior Publication Data
US 2017/0354966 A1    Dec. 14, 2017

Related U.S. Application Data

(60) Provisional application No. 62/341,426, filed on May 25, 2016.

(51) Int. Cl.
*B01L 3/02*     (2006.01)
*G01N 1/40*     (2006.01)
*C12N 15/10*    (2006.01)

(52) U.S. Cl.
CPC .......... *B01L 3/0275* (2013.01); *C12N 15/101* (2013.01); *C12N 15/1006* (2013.01);
(Continued)

(58) Field of Classification Search
CPC . B01L 3/022; B01L 2200/0631; G01N 1/405; Y10T 436/255
See application file for complete search history.

(56) References Cited

U.S. PATENT DOCUMENTS 5,582,988 A    12/1996   Backus et al.
6,048,457 A    4/2000    Kopaciewicz et al.
(Continued)

FOREIGN PATENT DOCUMENTS

EP    0707077 A2    4/1996

OTHER PUBLICATIONS

Viklund 1997 Chem Matr 9:463-471 (Year: 1997).*
(Continued)

*Primary Examiner* — Rebecca M Giere
(74) *Attorney, Agent, or Firm* — Nelson Mullins Riley & Scarborough LLP; Jane E. Remillard, Esq.; Jill Gorny Sloper, Esq.

(57) ABSTRACT

The present invention provides a disposable pipette tip for dispersive solid phase extraction (SPE) that allows for rapid, automatable purification of large biomolecules, such as nucleic acids, proteins and polypeptides without the need for additional tools such as centrifuges, magnetic plates or vacuum manifolds. The pipette tip is designed for optimal biomolecule isolation while maintaining sample integrity. Optimized methods of using the dispersive pipette extraction system for isolation of large biomolecules are also provided.

16 Claims, 14 Drawing Sheets

Specification includes a Sequence Listing.

(52) U.S. Cl.
CPC ......... *C12N 15/1017* (2013.01); *G01N 1/405* (2013.01); *B01L 2200/0631* (2013.01); *B01L 2300/069* (2013.01); *B01L 2300/12* (2013.01)

(56) References Cited

U.S. PATENT DOCUMENTS

| | | | |
|---|---|---|---|
| 6,200,474 B1 | 3/2001 | Kopaciewicz et al. | |
| 6,537,502 B1 | 3/2003 | Shukla et al. | |
| 6,566,145 B2* | 5/2003 | Brewer | B01L 3/0275 210/661 |
| 6,914,137 B2 | 7/2005 | Baker | |
| 7,759,112 B2 | 7/2010 | Belgrader | |
| 8,574,923 B2 | 11/2013 | Cooney et al. | |
| 2003/0130499 A1 | 7/2003 | Baker | |
| 2003/0232403 A1* | 12/2003 | Kellogg | B01F 13/0059 435/7.32 |
| 2006/0124551 A1 | 6/2006 | Gjerde et al. | |
| 2013/0046040 A1* | 2/2013 | Srinivasan | B01D 39/1661 521/143 |
| 2013/0338245 A1 | 12/2013 | Baker | |
| 2015/0011016 A1 | 1/2015 | Brewer | |

OTHER PUBLICATIONS

Cho, S. et al., "Efficient prefractionation of low-abundance proteins in human plasma and construction of a two-dimensional map," Proteomics, vol. 5: 3386-3396 (2005).

Cox, H.D., et al., "Detection of human insulin-like growth factor-1 in deer antler velvet supplements," Rapid Commun. Mass Spectrom., vol. 27:2170-2178 (2013).

Cox, H.D. et al., "Interlaboratory Agreement of Insulin-like Growth Factor Concentrations Measured by Mass Spectrometry," Clinical Chemistry, vol. 60:541-548 (2014).

Fila, J. et al., "Enrichment techniques employed in phosphoproteomics," Amino Acids vol. 43:1025-1047 (2012).

Filip, S. et al., "Comparison of Depletion Strategies for the Enrichment of Low-Abundance Proteins in Urine," PLOS One, DOI:10.1371/journal.pone.0133773. 20 page (2015).

Gianazza, E. et al., "With or without you—Proteomics with or without major plasma/serum proteins," Journal of Proteomics, vol. 140: 62-80 (2016).

Hankinson, S. et al., "Circulating concentrations of insulin-like growth factor I and risk of breast cancer," Lancet, vol. 351: 1393-1396 (1998).

Henning, A. et al., "An alternative method for serum protein depletion/enrichment by precipitation at mildly acidic pH values and low ionic strength," Proteomics, vol. 15: 1935-1940 (2015).

Hwang, S. et al., "Dispersive Pipette Extraction for Automated Enrichment of IGF-1 from Serum," MSACL Conference, Jan. 23-26, 2017, Poster Presentation, 1 page.

Hwang, S. et al., "Selective Enrichment of Peptides by Utilizing Dispersive Pipette Extraction on Automated Liquid Handler for High Throughput Discovery and Processing," ASMS (Sanibel) Conference, Jan. 19-22, 2017, Poster Presentation, 1 page.

Josic, D. et al., "Separation of proteins from human plasma by sample displacement chromatography in hydrophobic interaction mode," Electrophoresis, vol. 33(12):20 pages, doi:10.1002/elps.201200006. (2012).

Kay, R. et al., "A novel mass spectrometry-based method for determining insulin-like growth factor 1: assessment in a cohort of subjects with newly diagnosed acromegaly," Clinical Endocrinology, vol. 78: 424-430 (2013).

Kiyonami, R. et al., "Quantifying Peptides in Complex Mixtures with High Sensitivity and Precision Using a Targeted Approach with a Hybrid Linear Ion Trap-Orbitrap Mass Spectrometer," Thermo Fisher Scientific, Application Note: 557, 8 pages (2011).

Li, W. et al., "Facile synthesis of $Fe_3O_4$@$TiO_2$—$ZrO_2$ and its application in phosphopeptide enrichment," J. Mater. Chem. B, vol. 1: 1947-1961 (2013).

Li, Y. et al., "Novel $Fe_3O_4$@$TiO_2$—$ZrO_2$ Core-Shell Microspheres for Selective Enrichment of Phosphopeptides in Phosphoproteome Analysis," Journal of Proteome Research, vol. 7: 2526-2538 (2008).

Lund, R.D., "Analyzing the Effect of Pipette Tip Geometries on Fluid Velocity and Shear Strain Rate: Biomek Wide Bore vs. Standard Pipette Tips," Beckman Coulter Technical Information, 4 pages (2012).

M'Hamdi, H. et al., "Usefulness of IGF-1 serum levels as diagnostic marker of nasopharyngeal carcinoma," Immunobiology, vol. 221:1304-1308 (2016).

Mahn, A. et al., "Depletion of highly abundant proteins in blood plasma by hydrophobic interaction chromatography for proteomic analysis," Journal of Chromatography B, vol. 878: 1038-1044 (2010).

Mazanek, M. et al., "Titanium dioxide as a chemo-affinity solid phase in offline phosphopeptide chromatography prior to HPLC-MS/MS analysis," Nature Protocols, vol. 2(5): 1059-1069(2007).

Mohan, S. et al., "Development of a Simple Valid Method for the Complete Removal of Insulin-like Growth Factor (IGF)-Binding Proteins from IGFs in Human Serum and other Biological Fluids: Comparison with Acid-Ethanol Treatment and C18 Sep-Pak Separation," Journal of Clinical Endocrinology and Metabolism, vol. 80(2): 637-647 (1995).

Mullis, T. et al., "Affinity-based Dispersive Pipette Extraction for Automated Purification," SLAS Conference, Feb. 4-8, 2017, Poster Presentation, 1 page.

Nie, Y. et al., "Enhanced Recovery of Trypsin Digested Proteins Using Dispersive Pipette Extraction for Downstream Proteomic Analysis," MSACL Conference, Feb. 21-25, 2016, Poster Presentation, 1 page.

Palmisano, G. et al., "A Novel Method for the Simultaneous Enrichment, Identification, and Quantification of Phosphopeptides and Sialylated Glycopeptides Applied to a Temporal Profile of Mouse Brain Development," Molecular & Cellular Proteomics 11:10.1074/mcp.M112.017509, 1191-1202 ( 2012).

Rainer, M. et al., "Analysis of protein phosphorylation by monolithic extraction columns based on poly (divinylbenzene) containing embedded titanium dioxide and zirconium dioxide nano-powders," Proteomics, vol. 8: 4593-4602 (2008).

Thevis, M. et al., "Mass Spectrometry In Sports Drug Testing: Structure Characterization and Analytical Assays," Mass Spec Rev., vol. 26:79-107 (2007).

Thingholm, T. et al., "Highly selective enrichment of phosphorylate peptides using titanium dioxide," Nature Protocols, vol. 1(4): 1929-1935 (2006).

Yan, J. et al., "Facile synthesis of titania-zirconia monodisperse microspheres and application for phosphopeptides enrichment," Chem. Commun., vol. 20: 2929-2931 (2009).

Yan, J. et al., "Selective enrichment of glycopeptides/phosphopeptides using porous titania microspheres," Chem. Commun., vol. 46: 5488-5490 (2010).

Zhou, H. et al., "Robust phosphoproteome enrichment using monodisperse microsphere-based immobilized titanium (IV) ion affinity chromatography," Nature Protocols, vol. 8(3): 461-480 (2013).

Zhou, H. et al., "Zirconium Phosphonate-Modified Porous Silicon for Highly Specific Capture of Phosphopeptides and MALDI-TOF MS Analysis," Journal of Proteome Research, vol. 5: 2431-2437 (2006).

* cited by examiner

DISPERSIVE PIPETTE EXTRACTION SYSTEM FOR PURIFICATION OF LARGE BIOMOLECULES

CROSS-REFERENCE TO RELATED APPLICATIONS

This application claims the benefit of the filing date under 35 U.S.C. § 119(e) to U.S. Provisional Patent Application No. 62/341,426, filed May 25, 2016, the entire contents of which is incorporated herein by reference.

SEQUENCE LISTING

The instant application contains a Sequence Listing which has been submitted electronically in ASCII format and is hereby incorporated by reference in its entirety. Said ASCII copy, created on May 31, 2017, is named IMJ 003 Sequence.txt and is 1,879 bytes in size.

BACKGROUND OF THE INVENTION

High throughput purification of larger biomolecules, such as nucleic acids, proteins and peptides, is necessary for a wide variety of clinical assays and research applications. Numerous approaches for purifying nucleic acids, proteins and peptides have been described in the art, many of which are based on binding to a fixed sorbent packed at the narrow end of a pipette tip. While such approaches have been applied to purifying nucleic acids, proteins and peptides, these types of tips have lower recoveries and slower workflows due to clogging of the fixed bed, or improper packaging leading to voiding or channeling effects which leads to inconsistent recoveries.

Alternatively, biomolecules also have been purified by precipitation of the biomolecule (e.g., nucleic acid) out of a mixture or by physical separation of the biomolecule from a mixture, for example using magnetic beads. While such approaches are effective in isolating biomolecules, they can be time consuming and can require the use of specialized machinery, including centrifuges and/or magnetic plates.

Methods and systems for purifying nucleic acid have also been described in which the nucleic acid is isolated from a mixture by passing the mixture through a glass frit, such as a sintered glass frit, under conditions effective to separate the nucleic acids from the extraneous matter (U.S. Pat. No. 7,759,112). Pipette tip systems comprising a glass frit filter to which an analyte (e.g., nucleic acid) binds have also been described in the art (U.S. Pat. No. 8,574,923). Furthermore, other pipette tip-based extraction systems have been described in the art (see e.g., U.S. Pat. Nos. 6,048,457, 6,200,474, 6,537,502, U.S. Publication No. 2006/0124551).

A dispersive pipette tip system for solid phase extraction (SPE) has been described in which particles that bind an analyte are contained within the housing of the pipette tip such that they can travel freely within the tip, allowing for thorough mixing between the adsorptive particles and a sample solution (U.S. Pat. No. 6,566,145). Furthermore, advancement on this dispersive pipette tip system has been described in which the housing of the pipette tip also contains a baffle system that is shaped to introduce turbulent mixing of a liquid sample and resin that is aspirated into the pipette tip (U.S. Publication No. 2015/0011016). While these dispersive pipette tip systems offer benefits and advantages, their use in isolation of large biomolecules, which pose unique purification requirements, such as avoidance of fragmentation by shearing or sample foaming, as well as higher complexity and/or viscosity of the starting solution, have not been described.

Thus, there still exists a need for isolation devices and methods that allow for rapid, simple and automatable purification of large biomolecules that maintain sample integrity, for example without shearing of large nucleic acid such as genomic DNA.

SUMMARY OF THE INVENTION

The invention provides a dispersive pipette extraction system for solid phase extraction (SPE) wherein the pipette tip houses absorptive particles that bind biomolecules of interest, such as nucleic acids, proteins, polypeptides, peptides or phosphopeptides, and wherein these absorptive particles are freely moveable within the housing of the pipette tip during the extraction process, thereby improving the mixing of the sample solution containing the biomolecules with the absorptive particles and speeding up the binding of the biomolecules to the absorptive particles. The dispersive pipette tip of the invention has been designed for optimal purification of large biomolecules while maintaining sample integrity, e.g., minimizing shearing and fragmentation of nucleic acids or other large biomolecules, as well as foaming of the liquid sample inside the tip. In particular, both the architecture of the pipette tip and the structure of the flit/absorptive particle system within the pipette have been optimized for efficient purification of large biomolecules.

The pipette system and methods of use thereof of the disclosure offer numerous advantages. For example, the methods of using the dispersive pipette system for isolating biomolecules allow for rapid sample processing (batch processing speeds are approximately 15 minutes for up to 96 samples per batch, as compared to 25-45 minutes for traditional magnetic plate processing methods or several hours for other standard methods). Furthermore, the invention lowers the cost for isolating biomolecules, since it does not require additional tools (such as centrifuges, magnetic plates, plate transferring robotics or vacuum manifolds) and the cost of the biomolecule-binding absorptive particles is less than that of traditionally used magnetic beads. Still further, the methods of the invention are automatable, whereas many prior art purification methods are not.

Accordingly, in one aspect, the invention pertains to a pipette tip for solid phase extraction comprising:
  a housing having a proximal end with a lower opening having an inner diameter of at least 0.05 inches and a distal end with an upper opening dimensioned to fit on the end of a dispenser, wherein the housing has a first inflection point and a second inflection point, the second inflection point being located closer to the lower opening than the first inflection point, wherein a taper angle between the lower opening and the second inflection point is 5 degrees or less;
  a first frit inside the housing above the lower opening;
  a second frit inside the housing between the first frit and the upper opening; and
  a plurality of absorptive particles that bind a biomolecule of interest inside the housing and confined between the first frit and the second frit,
  wherein the absorptive particles and the second frit are spaced apart so as to form a void therebetween, and wherein the void is dimensioned so that the adsorptive particles can travel freely within the void allowing thorough mixing between the adsorptive particles and a sample solution when the sample solution is in the void.

In another aspect, the invention pertains to a pipette tip for solid phase extraction comprising:
- a housing having a proximal end with a lower opening adapted for passage of a liquid and a distal end with an upper opening dimensioned to fit on the end of a dispenser;
- a first frit inside the housing above the lower opening, the first frit: (i) being made of a material that does not bind a biomolecule of interest; (ii) having an average porosity; and (iii) having interconnecting channels having a diameter;
- a second frit inside the housing and positioned between the first frit and the upper opening and
- a plurality of absorptive particles that bind a biomolecule of interest inside the housing and confined between the first frit and the second frit, the absorptive particles having a diameter,
- wherein the absorptive particles and the second frit are spaced apart so as to form a void therebetween, and wherein the void is dimensioned so that the adsorptive particles can travel freely within the void allowing thorough mixing between the adsorptive particles and a sample solution when the sample solution is in the void; and
- wherein the average porosity of the first frit is greater than the diameter of the absorptive particles and the diameter of the interconnecting channels of the first frit is smaller than the diameter of the absorptive particles.

In yet another aspect, the invention pertains to a pipette tip for solid phase extraction comprising:
- a housing having a proximal end with a lower opening having an inner diameter of at least 0.05 inches and a distal end with an upper opening dimensioned to fit on the end of a dispenser, wherein the housing has a first inflection point and a second inflection point, the second inflection point being located closer to the lower opening than the first inflection point, wherein a taper angle between the lower opening and the second inflection point is 5 degrees or less;
- a first frit inside the housing above the lower opening, the first frit: (i) being made of a material that does not bind a biomolecule of interest; (ii) having an average porosity; and (iii) having interconnecting channels having a diameter;
- a second frit inside the housing and positioned between the first frit and the upper opening and
- a plurality of absorptive particles that bind the biomolecule of interest inside the housing and confined between the first frit and the second frit, the absorptive particles having a diameter,
- wherein the absorptive particles and the second frit are spaced apart so as to form a void therebetween, and wherein the void is dimensioned so that the adsorptive particles can travel freely within the void allowing thorough mixing between the adsorptive particles and a sample solution when the sample solution is in the void; and
- wherein the average porosity of the first frit is greater than the diameter of the absorptive particles and the diameter of the interconnecting channels of the first frit is smaller than the diameter of the absorptive particles.

In one embodiment, the first frit has an average porosity of 60-80 microns and the absorptive particles have a diameter of 40-70 microns. In one embodiment, the first frit has an average porosity of 70 microns. In another embodiment, the interconnecting channels of the first frit have a diameter of at least 5 microns. In various embodiments, the first flit is, for example, a porous polymer plug or a metal screen. For example, the first frit can be a polyethylene plug, a polypropylene/polyethylene plug or a fluorinated polyethylene plug. In one embodiment, the first frit is a porous polymer plug, e.g., a polyethylene plug or a fluorinated polyethylene plug, with an average porosity of 70 microns and interconnecting channels having a diameter of at least 20 microns. Additional embodiments of the dimensions of the first frit and the absorptive particles are described herein.

In one embodiment, the pipette tip further comprises a baffle system contained within the housing, wherein the baffle system is shaped to disrupt movement of the adsorptive particles when the sample solution is introduced into the housing.

In various embodiments, the dispenser is selected from the group consisting of a pipettor, a liquid dispensing apparatus, a robotic liquid dispensing apparatus and a piston head.

In various embodiments, the adsorptive particles comprise a material selected from the group consisting of hydroxylated materials, silica, derivitized silica including carboxylated silica, silica/glass materials, ceramic materials, modified polymeric materials, charge switchable resins, negatively charged resins, reverse phase resins, ion exchange resins and affinity resins. In one embodiment, the absorptive particles comprise a reverse phase resin selected from the group consisting of divinylbenzene (DVB) resins, C4 resins, C8 resins and C18 resins. In one embodiment, the absorptive particles comprise an ion exchange resin selected from the group consisting of weak anion exchange resins, weak cation exchange resins, strong anion exchange resins and strong cation exchange resins. In one embodiment, the absorptive particles comprise an affinity resin selected from the group consisting of a Protein A resin, a Protein G resin, an IMAC resin, an albumin affinity resin and a titanium oxide resin.

In one embodiment, the biomolecule is selected from the group consisting of nucleic acids, proteins, polypeptides, peptides and phosphopeptides.

In another aspect, the invention pertains to a method of purifying biomolecules of interest by dispersive solid phase extraction (SPE), the method comprising:
- providing a pipette tip of the invention;
- providing a sample solution comprising the biomolecules of interest;
- aspirating into the pipette tip the sample solution such that the biomolecules of interest within the sample solution adheres to the adsorptive particles;
- expelling the sample solution from the pipette tip;
- washing the absorptive particles;
- aspirating into the pipette tip an extraction solvent that dissociates the biomolecules of interest from the adsorptive particles; and
- expelling the extraction solvent and biomolecules of interest from the pipette tip to thereby purify the biomolecules of interest.

In another aspect, the invention pertains to a method of purifying biomolecules of interest by dispersive solid phase extraction (SPE), the method comprising:
- providing a pipette tip of the invention;
- providing a sample solution in a sample tube, the sample solution comprising the biomolecules of interest and an anti-foaming agent;
- aspirating into the pipette tip about 95% of the sample solution, wherein about 5% of the sample solution remains in the sample tube with the lower opening of the pipette tip remaining in contact with the 5% of the sample solution in the sample tube;

holding the about 95% of the sample solution in contact with the adsorptive particles in the pipette tip for at least 10 seconds such that the biomolecules of interest within the sample solution adheres to the adsorptive particles;

expelling the sample solution from the pipette tip;

washing the absorptive particles;

aspirating into the pipette tip an extraction solvent that dissociates the biomolecules of interest from the adsorptive particles, and expelling the extraction solvent and biomolecules of interest from the pipette tip to thereby purify the biomolecules of interest.

The sample solution can be, for example, serum, a cell lysate or mixture of biofluids containing biomolecules of interest. Other non-limiting examples of sample solutions include serum samples, plasma samples, buccal samples, blood samples, urine samples, amniotic fluid samples, chorionic villi samples, cultured cell samples, exosome samples, oral fluids samples, dried blood samples and pap smear samples. In one embodiment, the sample solution further comprises an anti-foaming agent, such as 10-30% primary or secondary alcohol.

In certain embodiments, the sample solution is provided in a sample tube and wherein about 95% of the sample solution is aspirated into the pipette tip and about 5% of the sample solution remains in the sample tube with the lower opening of the pipette tip remaining in contact with the 5% of the sample solution in the sample tube.

In certain embodiments, the sample solution is held in contact with the adsorptive particles for at least 10 seconds, e.g., for 10-30 seconds, within the pipette tip before expelling the sample solution.

In certain embodiments, the sample solution is aspirated into and expelled from the pipette tip more than one time, e.g., at least 2 times, or at least 3 times or at least 5 times or 5-10 times, before washing the absorptive particles. In one embodiment, the sample solution is held in contact with the adsorptive particles for at least 10 seconds, e.g., 10-30 seconds, within the pipette tip after each round of aspiration of the sample solution into the pipette tip.

In one embodiment, the method of purifying biomolecules of interest is carried out by an automated programmable robotic system to which the pipette tip is attached. In another embodiment, the automated programmable robotic system carries out the method simultaneously on a plurality of sample solutions using a plurality of pipette tips, such as 96 pipette tips configured for use with a standard 96-well plate.

The methods of the invention can be used to purify essentially any type of biomolecule of interest, including nucleic acids (including genomic DNA and RNA), proteins, polypeptides, peptides and phosphopeptides.

Other features and aspects of the invention are described in further detail herein.

BRIEF DESCRIPTION OF THE DRAWINGS

FIG. 1A shows a pipette tip with a shallow taper angle (7) and a wide lower opening. FIG. 1B shows a typical pipette tip design with a shallow taper along the main body of the tip (2) and a larger taper angle (3) at the first inflection point (4) to adjust the height of the tip and to provide a narrow opening at the lower end. FIG. 1C shows a schematic diagram of the dispersive SPE pipette system of the disclosure having a wide lower opening design to facilitate fitting of a porous frit. This tip has a taper angle along the main body of the tip (5) and two inflection points (6, 8). The first inflection point (6) can allow for a variety of taper angles (7) to accommodate the volume and length of the tip, whereas the second inflection point (8) allows for the introduction of a shallow taper angle (9) between the lower opening and the second inflection point (8).

FIG. 11A is a gel of bacterial lysates from seven different variants, with recombinant protein with a 6x His Tag (SEQ ID NO: 7) highlighted in the box. FIG. 11B is a gel of affinity-purified protein purified using the dispersive SPE pipette system.

DETAILED DESCRIPTION OF THE INVENTION

The structure of the dispersive pipette extraction system of the invention is very similar to that described in U.S. Pat. No. 6,566,145 and U.S. Publication 2015/0011016 (the entire contents of each of which, including all drawings, is specifically incorporated herein by reference), but with further modifications to adapt the system for optimal purification of large biomolecules while maintaining the integrity of the sample containing the biomolecules, e.g., avoiding significant shearing or fragmentation of the biomolecules. As used herein, the term "biomolecule" is intended to encompass molecules found in biological systems, e.g., cells, tissues, organisms, and in particular molecules comprised of nucleotides or amino acids, such as nucleic acids (including DNA, RNA, genomic DNA, mRNA), proteins (including immunoglobulins, albumin, hormones, cytokines and the like), polypeptides, peptides and phosphopeptides, as well as glycoproteins and proteoglycans. As used herein, a "peptide" refers to a molecule containing 2-20 amino acids, a "polypeptide" refers to a molecule containing greater than but less than 50 amino acids (i.e., 21-49 amino acids) and a "protein" refers to a molecule containing greater than 50 amino acids. As used herein, the term "large biomolecule" refers to nucleic acids, proteins and polypeptides, but is not intended to encompass peptides.

The overall structure of the dispersive pipette tip comprises:
  a housing having a proximal end with a lower opening and a distal end with an upper opening dimensioned to fit on the end of a dispenser;
  a first fit inside the housing above the lower opening;
  a second frit inside the housing between the first frit and the upper opening; and
  a plurality of absorptive particles that bind the biomolecule of interest inside the housing and confined between the first frit and the second frit,
  wherein the absorptive particles and the second frit are spaced apart so as to form a void therebetween, and wherein the void is dimensioned so that the adsorptive particles can travel freely within the void allowing thorough mixing between the adsorptive particles and a sample solution when the sample solution is in the void.

Figure 1C:
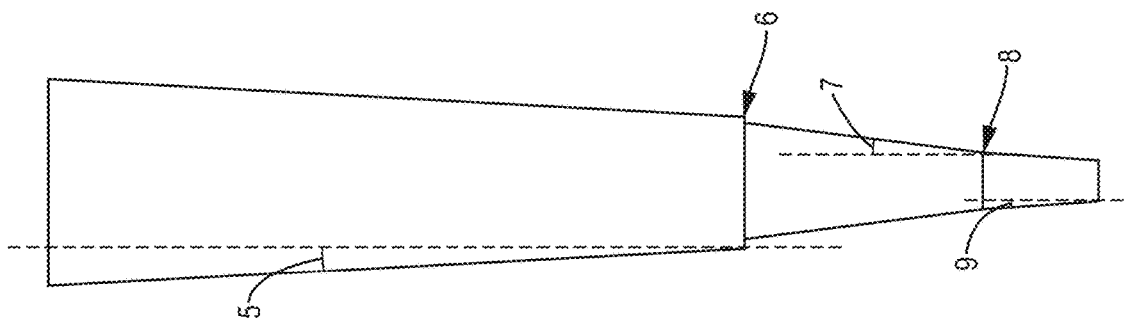
FIGS. 1A-C are schematic diagrams of the features of typical pipette tips and the dispersive SPE pipette system of the disclosure.
Figure 1B:
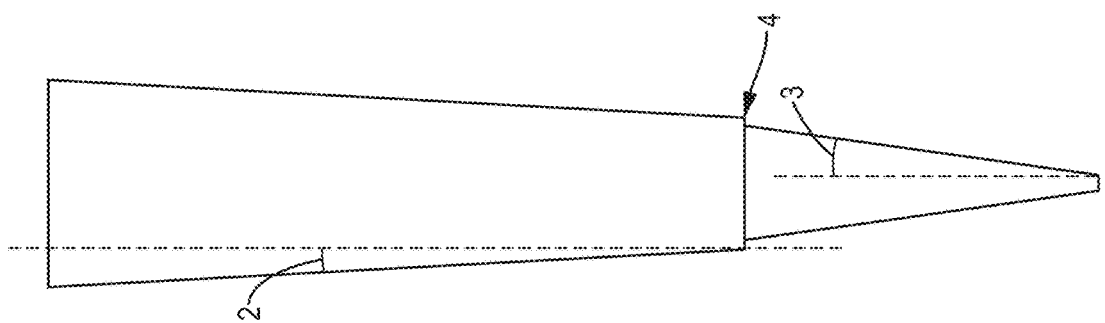
Figure 1A:
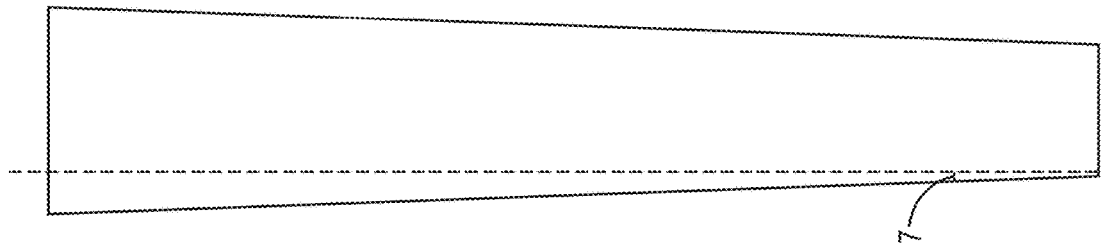

In a first modification for optimal biomolecule purification, the lower opening at the proximal end of pipette tip has been widened as compared to the prior art. More specifically, in the dispersive pipette tip of the invention, the lower opening has an inner diameter of at least 0.05 inches (1.27 mm) (see FIG. 1). In contrast, the inner diameter of standard pipette tips is approximately 0.6 mm (approximately 0.023 inches). The wider bore of the proximal end of the pipette tip serves to reduce shearing, fragmentation or other damage to biomolecules during aspirations. In various embodiments, the lower opening has a diameter of at least 0.05 inches (1.27 mm), at least 0.075 inches (1.90 mm) or at least 0.10 inch (2.54 mm). In one embodiment, the lower opening has a diameter of about 0.117 inches (2.97 mm) or of 0.117 inches (2.97 mm). In another embodiment, the lower opening has a diameter of about 3 mm or of 3 mm.

In another modification for optimal biomolecule purification, the shape of the pipette tip has been altered compared to the prior art. More specifically, in the dispersive tip of the invention, the housing forms a taper angle between the lower opening and the upper opening, or to an inflection point in the housing between the lower opening and the upper opening, wherein this taper angle is 5 degrees or less (see FIG. 1). In contrast, the taper angle of standard pipette tips is greater than 5 degrees. Thus, the pipette tip of the invention is straighter than standard pipette tips, which also serves to improve fitting of the first fit which is positioned above the lower opening and reduce instances where the frit may dislodge from the bottom opening. In particular embodiments, the pipette tip has a first inflection point (labeled 6 in FIG. 1C) and a second inflection point (labeled 8 in FIG. 1C), the second inflection point being located closer to the lower opening than the first inflection point. Furthermore, the taper angle between the lower opening and the second inflection point is 5 degrees or less, for example 5 degrees to 2 degrees, or 5 degrees to 1 degree, or 5 degrees, 4 degrees, 3 degrees, 2 degrees or 1 degree.

Figure 2:
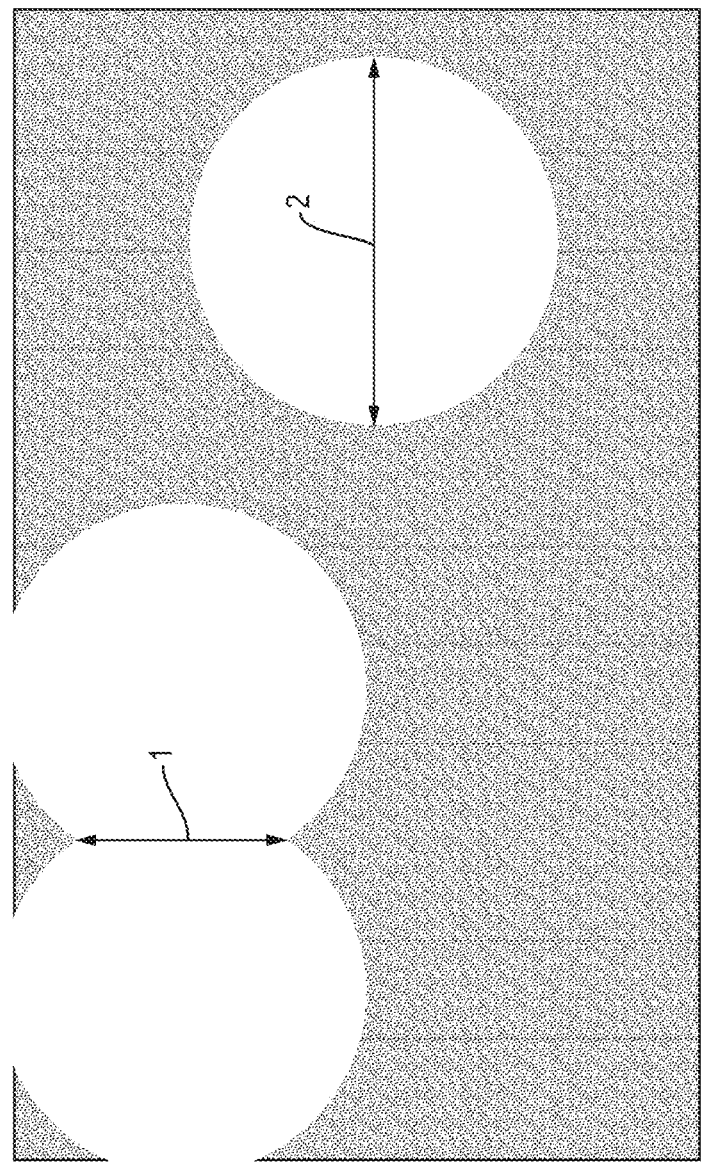
FIG. 2 is a schematic diagram of the porosity of the first frit, illustrating the length of the pore diameter (2) and the length of the interconnecting channels (1).

In another modification, the first frit, positioned above the lower opening, has been designed for optimal biomolecule purification, with respect to the absorptive particles contained within the pipette tip. More specifically, the first frit (i) is made of a material that does not bind the biomolecule of interest; (ii) has an average porosity; and (iii) has interconnecting channels having a diameter, wherein the average porosity of the first frit is greater than the diameter of the absorptive particles and the diameter of the interconnecting channels of the first frit is smaller than the diameter of the absorptive particles. As used herein, the term "interconnecting channels" is used in its art-recognized meaning with respect to materials, such as polymers, that have a porosity, in that it refers to the length of the opening (channel) formed between two pores (interconnecting two neighboring pores). The length of the pore diameter in the first frit and the length of the interconnecting channels in the first frit are illustrated schematically in FIG. 2. The average porosity of the material forming the first frit (e.g., polymer) is a parameter well established in the art (e.g., determined based on the average of the pore diameters within the material of the first frit).

The first frit serves as a "plug" to retain the absorptive particles within the housing of the pipette tip. Thus, it would be expected that the average porosity of the first frit must be smaller than the diameter of the absorptive particles to avoid loss of the absorptive particles from the housing. Surprisingly, however, it has been unexpectedly discovered that using a first frit having an average porosity that is greater than the diameter of the absorptive particles, wherein the diameter of the interconnecting channels of the first frit is smaller than the diameter of the absorptive particles, allows for retention of the absorptive particles within the housing while also allowing for effective passage of the biomolecule-containing sample solution (which can be viscous) through the first frit.

In one embodiment, the first frit has an average porosity of 60-80 microns and the absorptive particles have a diameter of 40-70 microns. In another embodiment, the first frit has an average porosity of 30-60 microns and the absorptive particles have a diameter of 20-50 microns. In one embodiment, the first frit has an average porosity of 30 microns or greater and the absorptive particles have a diameter of less than 30 microns, e.g., 20 microns. In another embodiment, the first frit has an average porosity of 40 microns or greater and the absorptive particles have a diameter of less than 40 microns, e.g., 30 microns. In another embodiment, the first frit has an average porosity of 50 microns or greater and the absorptive particles have a diameter of less than 50 microns, e.g., 40 microns. In another embodiment, the first frit has an average porosity of 60 microns or greater and the absorptive particles have a diameter of less than 60 microns, e.g., 50 microns. In another embodiment, the first frit has an average porosity of 70 microns or greater and the absorptive particles have a diameter of less than 70 microns, e.g., 60 microns. In another embodiment, the average porosity of the first frit is at least 10 microns larger than the diameter of the absorptive particles. In another embodiment, the average porosity of the first frit is 70 microns and the absorptive particles have a diameter of 40 microns.

In another embodiment, the interconnecting channels of the first frit have a diameter of at least 5 microns (wherein the absorptive particles have a diameter greater than the interconnecting channels). In another embodiment, the interconnecting channels of the first frit have a diameter of at least 10 microns (wherein the absorptive particles have a diameter greater than the interconnecting channels). In another embodiment, the interconnecting channels of the first frit have a diameter of at least 15 microns (wherein the absorptive particles have a diameter greater than the interconnecting channels). In another embodiment, the interconnecting channels of the first frit have a diameter of at least 20 microns (wherein the absorptive particles have a diameter greater than the interconnecting channels). In yet other embodiments, the interconnecting channels of the first frit have a diameter of 5 microns, or 10 microns, or 15 microns, or 20 microns (wherein the absorptive particles have a diameter greater than the interconnecting channels). In yet another embodiment, the interconnecting channels of the first frit have a diameter of 5-20 microns (wherein the absorptive particles have a diameter greater than the interconnecting channels).

The first frit used in the dispersive pipette system is made of a material that does not bind the biomolecule of interest. Thus, for example, for purification of nucleic acids, glass frits, e.g., sintered glass frits or glass wool frits, which do bind nucleic acids, are not suitable for use in the dispersive pipette system of the invention. Suitable material that does not bind biomolecules of interest that can be used for the first frit include, for example, a porous polymer plug or a metal screen. For example, the first frit can be a polyethylene plug, a polypropylene/polyethylene plug or a fluorinated polyethylene plug.

In certain embodiments, the first frit is held in place in the pipette tip by friction (i.e., connected to the housing by friction). Typically, the first frit is not physically attached to the housing of the pipette tip, although this embodiment is also encompassed by the invention.

The adsorptive particles comprise a material that binds the biomolecules of interest. This binding is a reversible binding such that under appropriate elution conditions, the biomolecules of interest can be dissociated from the adsorptive particles. In various embodiments, the adsorptive particles comprise a material selected from the group consisting of hydroxylated materials, silica, derivitized silica including carboxylated silica, silica/glass materials, ceramic materials, modified polymeric materials, charge switchable resins, negatively charged resins, reverse phase resins, ion exchange resins and affinity resins.

For purification of nucleic acids, examples of charge switchable or negatively charged resins that can be used include resins with ionizable groups that reversibly bind nucleic acid under different pH conditions, such as those described in U.S. Pat. No. 5,582,988, EP 0707077B1, U.S. Pat. No. 6,914,137, U.S. Publication No. 2003/0130499 and U.S. Publication No. 2013/0338245. For example, resins comprising histidine or polyhistidine groups, which bind nucleic acid at low pH (e.g., below pH 6) and release nucleic acid at high pH (e.g., above pH 8) (for example as described in U.S. Publication No. 2003/0130499) can be used as the absorptive particles.

For purification of proteins, polypeptides, peptides or phosphopeptides, a wide variety of absorptive particles known to bind such biomolecules are known in the art. For example, in one embodiment, the absorptive particles comprise a reverse phase resin, non-limiting examples of which include selected from the group consisting of divinylbenzene (DVB) resins (including DVB-styrene copolymers), C4 resins (including resins with a butyl side chain on a silica core, e.g., with a 500 Angstrom pore size), C8 resins (including resins with an octyl side chain on a silica core) and C18 resins (including resins with an octyldodecyl side chain on a silica core).

In another embodiment, the absorptive particles comprise an ion exchange resin, non-limiting examples of which include weak anion exchange resins (including polystyrene core modified with secondary amines), weak cation exchange resins (including carboxylate-conjugated polystyrene resins/beads), strong anion exchange resins (including quaternary amine-conjugated polystyrene resins/beads) and strong cation exchange resins (including sulfonic acid-conjugated polystyrene resins/beads).

In yet another embodiment, the absorptive particles comprise an affinity resin, non-limiting examples of which include Protein A resins, Protein G resins, Immobilized Metal Affinity Chromatography (IMAC) resins (including Cobalt-IMAC, Nickel-IMAC and Copper-IMAC resins), albumin affinity resins and titanium oxide ($TiO_2$) resins.

The pipette tip can be fashioned in various sizes, depending on the desired use. For example, in various embodiments, the pipette tip has a volume of 0.1-2.0 ml, or a volume of 0.1 ml, or a volume of 0.2 ml, or a volume of 0.3 ml, or a volume of 0.4 ml, or a volume of 0.5 ml, or a volume of 0.6 ml, or a volume of 0.7 ml or a volume of 0.8 ml, or a volume of 0.9 ml, or a volume of 1.0 ml, or a volume of 1.5 ml or a volume of 2.0 ml.

In one embodiment, the pipette tip further comprises a baffle system contained within the housing, wherein the baffle system is shaped to disrupt movement of the adsorptive particles when the sample solution is introduced into the housing. Suitable baffle systems are described in detail in U.S. Publication No. 2015/0011016. Non-limiting examples of types of baffles that can be used include fins, O-rings and blades. In a preferred embodiment, the baffle system, such as fins, is built into the pipette tip, although baffle systems (such as O-rings or blades) that are inserted into the pipette tip can also be used.

The upper opening at the distal end of the dispersive pipette tip is dimensioned to fit on the end of a dispenser. In various embodiments, the dispenser is selected from the group consisting of a pipettor (e.g., a standard manual laboratory pipettor or an electronic pipettor), a liquid dispensing apparatus, a robotic liquid dispensing apparatus and a piston head. Suitable dispensers are known and available in the art.

The second frit is optional. The purpose of second frit is to prevent the passage of either solids or fluids therethrough and thus any material suitable for this purpose can be used for the second frit. The second frit insures the retention of the absorptive particles within the housing of the pipette tip and prevents contamination of the pipettor by sample solution or solvents during the agitation step. The second frit can be, for example, a sintered glass plug, a porous polymer plug, or a semi-permeable membrane.

The housing of the pipette tip can be made of any inexpensive material or commodity plastic, but is preferably made from a polyolefin, and most preferably made from polyethylene, polypropylene, polyethylene-terephthalate or polytetrafluoroethylene.

The various features of the dispersive pipette tip system described herein that have been optimized for biomolecule purification (including the wide bore of the lower opening, the narrow angle of the tapering angle of the housing, and the dimension specificities of the first frit and the absorptive particles) can be used in the pipette tip singly or in combination. All possible combinations of these features are intended to be encompassed by the invention.

The dispersive pipette tips of the invention can be used in methods of purifying biomolecules of interest by dispersive solid phase extraction (SPE). With respect to the purification methods, and pipette tip system used therein, as described herein, the terms "a biomolecule of interest" and "biomolecules of interest" are used interchangeably, and refer to the collective pool of biomolecules that are purified from a sample solution using the pipette tip system described herein.

The purification method typically comprises:
providing a pipette tip of the invention;
providing a sample solution comprising the biomolecules of interest;
aspirating into the pipette tip the sample solution such that the biomolecules of interest within the sample solution adheres to the adsorptive particles;
expelling the sample solution from the pipette tip;
washing the absorptive particles;
aspirating into the pipette tip an extraction solvent that dissociates the biomolecules of interest from the adsorptive particles; and
expelling the extraction solvent and biomolecules of interest from the pipette tip to thereby purify the biomolecules of interest.

The purification method can include additional aspects and features that have been discovered to optimize biomolecule purification while maintaining sample integrity, e.g., minimizing shearing and/or fragmentation using the dispersive pipette tip. One additional such feature is that is has been discovered that holding the sample solution in contact with the absorptive particles, following aspiration, for at least 10 seconds before expelling the sample solution improves biomolecule binding and recovery. Accordingly, in various embodiments, the sample solution is held in contact with the adsorptive particles in the pipette tip for at least 10 seconds, or for 10-30 seconds, or for at least 15 seconds, or at least 20 seconds, or at least 25 seconds, or at least 30 seconds, such that the biomolecules within the sample solution adhere to the adsorptive particles, before expelling the sample solution and carrying out the washing step(s).

Another additional optimization feature of the purification method is that is has been discovered that aspirating the sample solution into the pipette tip more than two times improves biomolecule binding and recovery. Accordingly, in various embodiments, the sample solution is aspirated at least three times, at least four times, at least five times, at least six times, at least seven times, at least eight times, at least nine times, at least 10 times or 5-10 times, 10-15 times or 20 times into the housing of the pipette tip, before washing the absorptive particles. Furthermore, the method can include a hold period (e.g., seconds, 10-30 seconds) between each round of aspirating/dispensing of the sample solution (before the washing step(s)) to enhance the binding of the biomolecules to the absorptive particles.

Yet another additional optimization feature of the purification method is that is has been discovered that aspirating less than 100% of the sample solution into the pipette tip, such that a small portion of the sample solution remains in the sample tube, reduces foaming of the solution, optimizes aspiration efficiency and enhances biomolecule purification while reducing biomolecule shearing. Accordingly, in certain embodiments, the sample solution is provided in a sample tube and about 95% of the sample solution is aspirated into the pipette tip and about 5% of the sample solution remains in the sample tube with the lower opening of the pipette tip remaining in contact with the 5% of the sample solution in the sample tube. As used herein the term "about" is intended to encompass a minimal variation from the stated percentage that does not significantly affect the performance or outcome of the method (e.g., about 96% of the sample solution can be aspirated and about 4% of the sample solution can remain in the sample tube, or about 94% of the sample solution can be aspirated and about 6% of the sample solution can remain in the sample tube, and the like). The % of the sample solution aspirated into the pipette tip is selected to be high enough to ensure efficient biomolecule recovery from the sample while leaving a minimal amount of the sample in the sample tube to prevent foaming and to optimize aspiration efficiency.

The sample solution can be, for example, serum, a cell lysate or mixture of biofluids containing biomolecules of interest. Non-limiting examples of sample solutions include serum samples, plasma samples, buccal samples, blood samples, urine samples, amniotic fluid samples, chorionic villi samples, cultured cell samples, exosome samples, oral fluids samples, dried blood samples and pap smear samples. In one embodiment, the sample solution further comprises an anti-foaming agent, such as 10-30% primary or secondary alcohol.

Suitable solutions for lysing cell samples, for washing the absorptive particles and for extracting (eluting) the biomolecules from the absorptive particles are well known in the art. Non-limiting examples of suitable solutions are described in the Examples. Depending on the nature of the absorptive particles used in the pipette tip, the ordinarily skilled artisan can readily choose the appropriate washing and extracting solutions to use for biomolecule purification. A single washing step can be performed or, alternatively, multiple washing steps can be performed.

In one embodiment, the method of purifying the biomolecules of interest is carried out by an automated programmable robotic system to which the pipette tip is attached. In another embodiment, the automated programmable robotic system carries out the method simultaneously on a plurality of sample solutions using a plurality of pipette tips, such as 96 pipette tips configured for use with a standard 96-well plate. Suitable automated dispensing systems for use with the dispersive pipette tips and methods of the invention are known in the art.

The methods of the invention for nucleic acid purification can be used to purify essentially any type of nucleic acid, non-limiting examples of which include genomic DNA and RNA. Other types of nucleic acid that can be purified include cDNA, bacterial DNA, viral DNA, plasmid DNA and the like.

The various features of the purification methods described herein that have been optimized for biomolecule purification (including the holding of the sample solution in contact with the absorptive particles for a period of time, the use of multiple rounds of aspirating/dispensing before the washing step, the aspiration of only a portion, e.g., 95%, of the sample solution into the pipette tip and the use of anti-foaming agent) can be used in the purification methods singly or in combination. All possible combinations of these features are intended to be encompassed by the invention.

For example, in another aspect, the invention pertains to a method of purifying a biomolecule of interest by dispersive solid phase extraction (SPE), the method comprising:

providing a pipette tip of the invention;

providing a sample solution in a sample tube, the sample solution comprising nucleic acid and an anti-foaming agent;

aspirating into the pipette tip about 95% of the sample solution, wherein about 5% of the sample solution remains in the sample tube with the lower opening of the pipette tip remaining in contact with the 5% of the sample solution in the sample tube; holding the about 95% of the sample solution in contact with the adsorptive particles in the pipette tip for at least 10 seconds such that the biomolecule of interest within the sample solution adheres to the adsorptive particles;

expelling the sample solution from the pipette tip;

washing the adsorptive particles;

aspirating into the pipette tip an extraction solvent that dissociates the biomolecule of interest from the adsorptive particles; and expelling the extraction solvent and biomolecule of interest from the pipette tip to thereby purify the biomolecule of interest.

In one embodiment, the sample solution comprises 10-30% primary or secondary alcohol as the anti-foaming agent.

In another embodiment, about 95% of the sample solution is held in contact with the adsorptive particles for about 10-30 seconds within the pipette tip before expelling the sample solution.

In another embodiment, about 95% of the sample solution is aspirated into and expelled from the pipette tip at least 2 times or at least 3 times, or at least 5 times or at least 5-10 times, before washing the adsorptive particles, the about 95% of the sample solution being held in contact with the adsorptive particles for at least 10 seconds (e.g., 10-30 seconds) within the pipette tip after each aspiration of the about 95% of the sample solution into the pipette tip.

In certain embodiments, the disclosure provides methods for purification of particular biomolecules of interest using the dispersive SPE pipette system. For example, in one embodiment, the biomolecule of interest is nucleic acid. Specific conditions for nucleic acid purification are described in detail in Example 1.

In another embodiment, the invention provides a method of enriching proteins in a serum sample, such as a depleted serum sample. As used herein, a "depleted serum sample" refers to a serum sample in which the most abundant serum proteins (e.g., albumin, immunoglobulin) have been removed, yet which still contains a range of serum proteins of different sizes and abundance. Enrichment for less abundant serum proteins is highly desirable for the discovery of biomarkers and for disease detection. As described in detail in Example 3, the dispersive SPE pipette system has been effectively used to enrich for less abundant serum proteins. Thus, in this situation, the "biomolecules of interest" that are purified using the pipette system and methods of the disclosure are serum proteins (e.g., low abundance serum proteins).

Accordingly, in another aspect, the invention provides a method of enriching serum proteins (e.g., low abundance serum proteins), the method comprising:

providing a pipette tip of the invention (e.g., wherein the absorptive particles therein are a reverse phase resin, such as a C4 reverse phase resin);

providing a serum sample (e.g., a depleted serum sample);

aspirating into the pipette tip the serum sample such that the serum proteins of interest within the sample solution adhere to the adsorptive particles;

expelling the serum sample from the pipette tip;

washing the absorptive particles;

aspirating into the pipette tip an extraction solvent that dissociates the serum proteins of interest from the adsorptive particles; and expelling the extraction solvent and serum proteins of interest from the pipette tip to thereby purify the serum proteins of interest.

In one embodiment, prior to aspirating the serum sample into the pipette tip, the pipette tip is conditioned, first with 100% methanol, then with a basic solution (e.g., 5% ammonium hydroxide or IM sodium hydroxide). In one embodiment, the pipette tip is washed with 0.1% fluoroacetic acid (FA). In one embodiment, the extraction solvent is an isopropanol/methanol/acetone solution. Additional non-limiting specific conditions and solutions for enrichment of serum proteins are described in Example 3.

In another embodiment, the invention provides a method of purifying IGF-1 from a biological sample, such as a serum sample. Purification of IGF-1 from biological samples is desirable in a number of clinical situations, as described in detail in Example 4. As described in detail in Example 4, the dispersive SPE pipette system has been effectively used to purify IGF-1 from serum samples. Thus, in this situation, the "biomolecule of interest" that is purified using the pipette system and methods of the disclosure is IGF-1.

Accordingly, in another aspect, the invention provides a method of purifying IGF-1, the method comprising:

providing a pipette tip of the invention (e.g., wherein the absorptive particles therein are a reverse phase resin, such as a DVB-polystyrene reverse phase resin);

providing a biological sample containing IGF-1 (e.g., a serum sample);

aspirating into the pipette tip the biological sample such that IGF-1 within the biological sample adheres to the adsorptive particles;

expelling the biological sample from the pipette tip;

washing the absorptive particles;

aspirating into the pipette tip an extraction solvent that dissociates IGF-1 from the adsorptive particles; and expelling the extraction solvent and IGF-1 from the pipette tip to thereby purify IGF-1.

In one embodiment, prior to aspirating the biological sample into the pipette tip, the pipette tip is conditioned with 100% acetonitrile. In one embodiment, the serum is bound to the pipette tip in a binding buffer of 10% acetonitrile, 2% acetic acid (pH 3). In another embodiment, the pipette tip is washed with 10% acetonitrile, 2% acetic acid (pH 3). In one embodiment, the extraction solvent is acidified methanol. In another embodiment, the extraction solvent is 70 acetonitrile, 100 mM ammonium bicarbonate buffer. Additional non-limiting specific conditions and solutions for purification of IGF-1 are described in Example 4.

In another embodiment, the invention provides a method of purifying a His-tagged protein from a biological sample, such as a cell lysate. His-tags are extensively used for labeling proteins and, thus, rapid and efficient methods for purifying His-tagged proteins are highly desirable. As described in detail in Example 5, the dispersive SPE pipette system has been effectively used to purify a His-tagged protein from a cell lysate (e.g., bacterial cell lysate). Thus, in this situation, the "biomolecule of interest" that is purified using the pipette system and methods of the disclosure is a His-tagged protein.

Accordingly, in another aspect, the invention provides a method of purifying a His-tagged protein, the method comprising:

providing a pipette tip of the invention (e.g., wherein the absorptive particles therein are an IMAC resin, such as a Cobalt-IMAC resin);

providing a biological sample containing a His-tagged protein (e.g., cell lysate);

aspirating into the pipette tip the biological sample such that the His-tagged protein within the biological sample adheres to the adsorptive particles;

expelling the biological sample from the pipette tip;

washing the absorptive particles;

aspirating into the pipette tip an extraction solvent that dissociates the His-tagged protein from the adsorptive particles; and expelling the extraction solvent and His-tagged protein from the pipette tip to thereby purify the His-tagged protein.

In one embodiment, prior to aspirating the biological sample into the pipette tip, the pipette tip is conditioned with 20 mM sodium phosphate, 0.5 M NaCl, 20-40 mM imidazole, pH 7.4. In one embodiment, the pipette tip is washed with this same solution. In one embodiment, the extraction solvent is 20 mM sodium phosphate, 0.5 M NaCl, 500 mM imidazole, pH 7.4. Additional non-limiting specific conditions and solutions for purification of His-tagged proteins are described in Example 5.

In another embodiment, the invention provides a method of purifying immunoglobulin (e.g., IgG) from a biological sample, such as serum. Purification of immunoglobulin is desirable in a variety of clinical situations. As described in detail in Example 6, the dispersive SPE pipette system has been effectively used to purify immunoglobulin from serum. Thus, in this situation, the "biomolecule of interest" that is purified using the pipette system and methods of the disclosure is immunoglobulin (e.g., IgG).

Accordingly, in another aspect, the invention provides a method of purifying immunoglobulin, the method comprising:

providing a pipette tip of the invention (e.g., wherein the absorptive particles therein are an immunoglobulin affinity resin, such as a Protein A or Protein G resin);

providing a biological sample containing immunoglobulin (e.g., serum);

aspirating into the pipette tip the biological sample such that the immunoglobulin within the biological sample adheres to the adsorptive particles;

expelling the biological sample from the pipette tip;

washing the absorptive particles;

aspirating into the pipette tip an extraction solvent that dissociates the immunoglobulin protein from the adsorptive particles; and expelling the extraction solvent and immunoglobulin from the pipette tip to thereby purify the immunoglobulin.

In one embodiment, prior to aspirating the biological sample into the pipette tip, the pipette tip is conditioned with 20 mM sodium phosphate, 0.15 M sodium chloride. In one embodiment, the pipette tip is washed with this same solution. In one embodiment, the extraction solvent is 0.1 M sodium citrate, pH 3.5. In one embodiment, after elution, the sample is neutralized with 1 M Tris, pH 9.0. Additional non-limiting specific conditions and solutions for purification of immunoglobulin are described in Example 6.

In another embodiment, the invention provides a method of purifying phosphopeptides from a sample solution. As described in detail in Example 7, the dispersive SPE pipette system has been effectively used to purify phosphopeptides from a sample solution. Use of the dispersive SPE pipette system for phosphopeptide purification allowed for higher specificity, lower background and for direct MS analysis without the need for a post-cleanup step. Thus, in this situation, the "biomolecules of interest" that are purified using the pipette system and methods of the disclosure are phosphopeptides.

Accordingly, in another aspect, the invention provides a method of purifying phosphopeptides, the method comprising:

providing a pipette tip of the invention (e.g., wherein the absorptive particles therein are a phosphopeptide affinity resin, such as a $TiO_2$ resin);

providing a sample solution containing phosphopeptides;

aspirating into the pipette tip the sample solution such that the phosphopeptides within the sample solution adhere to the adsorptive particles;

expelling the sample solution from the pipette tip;

washing the absorptive particles;

aspirating into the pipette tip an extraction solvent that dissociates the phosphopeptides from the adsorptive particles; and expelling the extraction solvent and phosphopeptides from the pipette tip to thereby purify the phosphopeptides.

In one embodiment, prior to aspirating the biological sample into the pipette tip, the pipette tip is activated with 100% acetonitrile (ACN) and conditioned with 80% ACN, 0.4% trifluoroacetic acid (TFA). In one embodiment, after conditioning, the pipette tip is equilibrated with, for example, 25% lactic acid, 60% ACN, 0.3% TFA. In one embodiment, the sample is applied to the pipette tip in, for example, 25% lactic acid, 60% ACN, 0.3% TFA. In one embodiment, the pipette tip is washed with, for example, 25% lactic acid, 60% ACN, 0.3% TFA. In one embodiment, the pipette tip is washed (or further washed) with, for example, 80% ACN, 0.4% TFA. In one embodiment, the extraction solvent is, for example, 1.5% $NH_4OH$, 10% ACN. In one embodiment, after elution, the sample is reconstituted in, for example, 0.1% formic acid. In one embodiment, the sample is analyzed by mass spectrometry after reconstitution, without need for any further sample preparation. Additional non-limiting specific conditions and solutions for purification of phosphopeptides are described in Example 7.

In yet another embodiment, the invention provides a method of depleting proteins from a serum sample. As described in detail in Example 8, the dispersive SPE pipette system has been effectively used to deplete proteins from a serum sample, resulting in removal of over 99% of protein from serum while still retaining many of the smaller molecules in the flow through. Thus, in this situation, the "biomolecules of interest" that are purified using the pipette system (i.e., the biomolecules in the sample that bind to the absorptive particles) are the proteins within the serum sample that one wishes to deplete from the serum sample. In this situation, however, the smaller molecules in the flow through (e.g., lower abundance serum molecules) may be of interest to collect and retain for use in further analyses.

Accordingly, in another aspect, the invention provides a method of preparing a protein-depleted serum sample, the method comprising:

providing a pipette tip of the invention (e.g., wherein the absorptive particles therein are a reverse phase resin, such as a C4 reverse phase resin);

providing a serum sample;

aspirating into the pipette tip the serum sample such that proteins within the serum sample adhere to the adsorptive particles; and expelling the serum sample from the pipette tip to thereby obtain a protein-depleted serum sample. This protein-depleted serum sample can then be used for further analysis of the lower abundance molecules that remain in the flow through.

The method can further comprise:

washing the absorptive particles;

aspirating into the pipette tip an extraction solvent that dissociates the bound serum proteins from the adsorptive particles; and expelling the extraction solvent and serum proteins from the pipette tip to thereby purify the bound serum proteins.

In one embodiment, prior to aspirating the serum sample into the pipette tip, the pipette tip is conditioned with 100% isopropanol. In another embodiment, after aspiration of the serum into the pipette tip, 100% isopropanol is aspirated into the tip (for a "protein crash" method that precipitates the proteins to further promote depletion from the serum). Additional non-limiting specific conditions and solutions for depletion of proteins from serum samples are described in Example 8.

The present invention is further illustrated by the following examples, which should not be construed as further limiting. The contents of Sequence Listing, figures and all references, patents and published patent applications cited throughout this application are expressly incorporated herein by reference.

EXAMPLES

Example 1: DNA Isolation Using Dispersive SPE Pipette System

In this example, genomic DNA from buccal swabs was isolated using the dispersive SPE pipette system and methodologies of the invention, as compared to two other commercially available DNA extraction kits. One of the commercially available DNA extraction kits isolates DNA using magnetic beads that bind DNA, whereas the other commercially available DNA extraction kit isolates DNA by precipitating the DNA.

Buccal Swab Samples

Buccal swab samples were obtained from 4 participants. Each swab was immediately processed for isolation of DNA. The swabs were collected from volunteers who signed an informed consent document. All samples were collected using the CytoSoft Cytology brush. The participants all self-swabbed and were instructed to swab 10 times on each check. The participants were also asked to not eat one hour prior to performing cheek swabs. All samples were processed immediately after sample was taken. Purified DNA solution was stored at −20° C. in a 1.5 mL Eppendorf tube.

DNA Extraction from Buccal Swab

Three replicates of three different extraction methods were tested by obtaining a pooled genomic DNA (gDNA) sample from 9 cytology brushes. The 9 brushes were used to obtain cells from four different volunteers. All 9 brushes were combined and processed as one prior to aliquoting into 9 separate 1.5 mL centrifuge tubes. The brushes were incubated with a total of 1.8 mL of elution buffer and 1.8 mL of lysis buffer (Omega biotek) and 200 μL of proteinase K (New England Biolabs) for 15 minutes at 55° C. Three of the samples were processed using magnetic beads to bind and elute the DNA, three of the samples were processed using a kit that precipitates the DNA. For both of these kits the samples were processed following the manufacturer's instructions. The last three samples were processed using the dispersive SPE pipette system of the invention following the protocol described below, which is able to be fully automated without a magnetic manifold or centrifugation.

DNA Isolation by Dispersive SPE

To isolate genomic DNA from the buccal swab samples using the dispersive SPE pipette system of the invention, 300 μl of 100% isopropanol was added to the lysates and mixed. The pipette tips of the invention were connected to a pipettor or to a liquid handler and 250 μl of 250 mM sodium hydroxide was aspirated into and dispensed from the pipette tips twice to condition the tips. The lysates were then aspirated into and dispensed from the pipette tips, typically 5-10 times, with a 10-30 second hold between each round of aspirating/dispensing. This hold allows the sample to mix inside the tip with the resin and then allows the resin to settle out of solution to the bottom of the pipette tip. The pipette tips (with DNA bound to the resin therein) were then washed twice with 250 μl of 70% ethanol. An optional third wash can be performed by aspirating/dispensing with 250 μl of 100% acetone. The pipette tips were then air aspirated 15 times to dry down the tip, and then the bound genomic DNA was eluted with 100 μl of elution buffer (10 mM TE pH 8) by holding the elution buffer in the tip for 1-2 minutes prior to dispensing. Elution can be done at room temperature or, alternatively, elution at higher temperatures (e.g., 37° C. or 50-60° C.) improves genomic DNA recovery.

Yield of Total Extracted DNA

The yield of the total extracted DNA was determined using the Quant-It™ PicoGreen (Life Technologies) assay according to the vendor's protocol. The main purpose of this study was to compare the different kits' abilities to isolate DNA from buccal swabs. Further, the different binding technologies were selected purposefully in order to compare DNA recoveries from buccal swabs. In order to give an accurate comparison of the kit's ability to isolate DNA, once the cells had been lysed, the cells were pooled into one lysate. This means that each starting sample had the same amount of DNA present. For all three kits a final elution volume of 100 μL was used to elute the DNA. The total DNA recoveries varied from kit to kit, but stayed within a reasonable range of 968 ng to 2106 ng based on PicoGreen.

Total Yield of Genomic DNA

The technology used to isolate DNA from buccal swabs binds all DNA present in the sample. This means that contaminating bacterial DNA present in the sample will be isolated along with human gDNA. PicoGreen is not able to discriminate between bacterial DNA and human gDNA due to its affinity to bind to all DNA. Thus, in order to determine the amount of human gDNA isolated in each sample, a SYBR Green qPCR assay with a human GAPDH primer set (Integrated DNA Technologies) was used. The following forward and reverse GAPDH PCR oligonucleotide primers, which produce a 120 bp amplicon, were used:

(SEQ ID NO: 1)
GAPDH Gene Forward: 5'-CTCTGCTCCTCCTGTTCGAC-3'

(SEQ ID NO: 2)
GAPDH Gene Reverse: 5'-TTCCCGTTCTCAGCCTTGAC-3'

Figure 3:
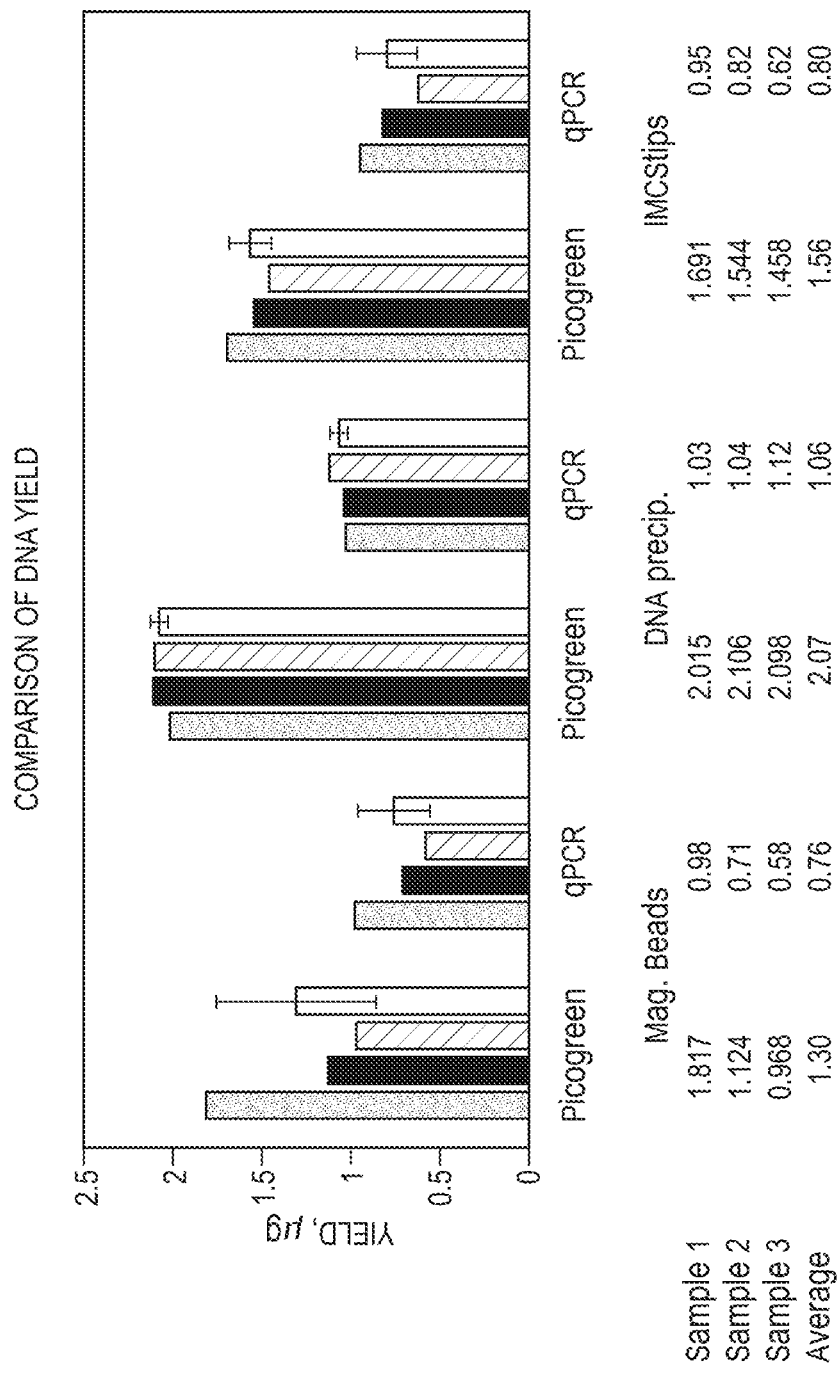
FIG. 3 is a series of bar graphs, and quantitative values therefor, comparing total DNA yields, as determined by PicoGreen, and genomic DNA yields, as determined by qPCR, using three different DNA isolation technologies.

For the qPCR reactions, a master-mix of 2×SYBR Green (10 μL), 2 μM forward/reverse primers (2 μL), and water (6 μL) with 2 μL of gDNA sample were used. As a positive control, human male DNA (Promega, PR-G1471) was used. The cycling conditions were: 95° C. 10 minutes, then 40 cycles of 95° C. for 15 seconds, 60° C. for 30 seconds and 72° C. for 30 seconds. The positive control was used to make a standard curve making several dilutions from a starting gDNA concentration of 1 ng/μL, and a total of four standards were used. Along with the standards, samples that had been diluted to 1 ng/μL of DNA based on the PicoGreen were loaded in duplicate and then quantified based on the standard curve. A melt curve, obtained by ramping from 72° C. to 95° C. at 0.3° C. per second, indicated all PCR runs were amplifying a single target. The results are shown in FIG. 3, which compares the yield of total DNA, as determined by PicoGreen, with the yield of genomic DNA, as determined by qPCR, for the three DNA isolation technologies used. Based on the qPCR assay, the recovery of gDNA ranged from 578 ng to 1124 ng.

DNA Integrity

Figure 4:
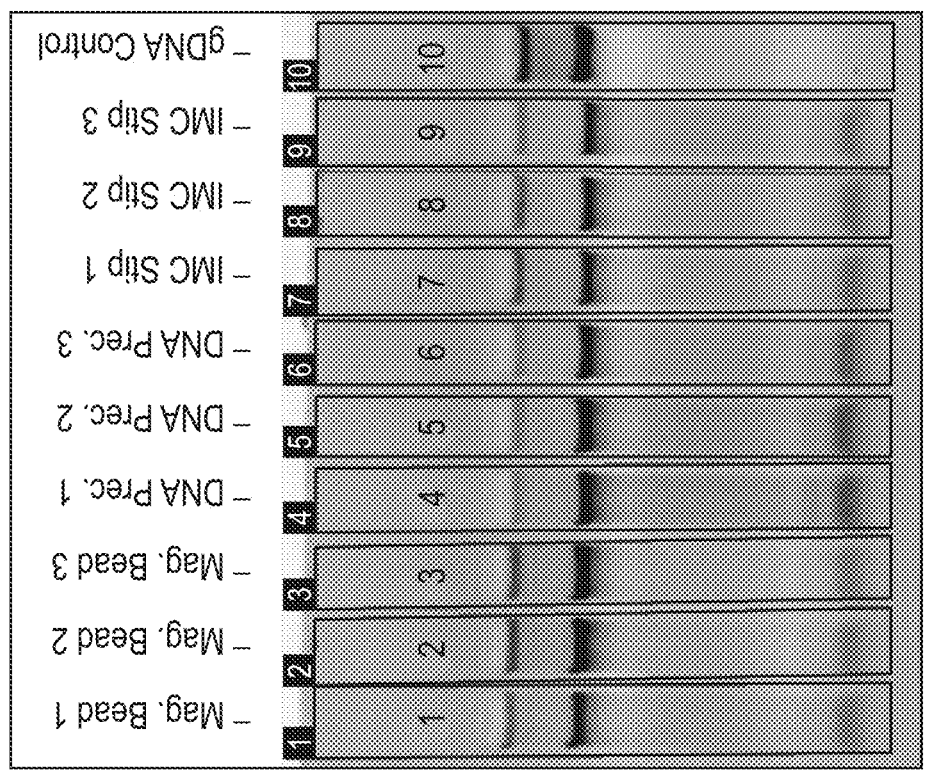
FIG. 4 is an image of an agarose gel comparing DNA integrity of genomic DNA isolated using three different DNA isolation technologies.

In order to determine the integrity of the genomic DNA extracted from the swabs, an agarose gel was run in order to obtain a gel image of the DNA. The integrity of the gDNA was determined by Nucleic Acid Electrophoresis using BIO-RAD Mini-Sub Cell GT with a Fisher Biotech FB300 power supply. Bio-Rad Ready Agarose Gels were used along with Thermo 6×DNA loading dye (ThermoFisher Scientific, R0611) to run the samples. A total of 100 ng of DNA (quantified by PicoGreen) was loaded into each lane from the 9 different purified samples (3 samples for each of the three different purification technologies). As a comparison, a standard of 100 ng of gDNA (Promega) was run on the gel. The samples were run at a standard setting of 100 V, 375 mA, 30 mins. The gel was imaged using an Amersham Imager 600 (GE Healthcare Life Sciences). The results are shown in FIG. 4, which demonstrate that the majority of the DNA isolated by the kits was high molecular weight DNA. The difference between the standard gDNA and the samples can be attributed to co-extracted bacterial DNA and fragmented DNA.

Detection of the Presence of qPCR Inhibitors in Purified Samples

The purpose of the DNA purification kits is to produce a PCR ready purified sample. In order to determine if this was produced by the samples, the presence of PCR inhibitors was tested for experimentally using qPCR. PCR inhibitors are any contaminants that inhibits the amplification process in the PCR. The purified samples were tested for the presence of qPCR amplification inhibitors by running four 2× serial dilutions of the sample starting with a DNA concentration of 1 ng/μL. As a reference sample, the same four 2× serial dilutions were carried out on the standard gDNA (Promega, PR-G1471) starting at a 1 ng/μL. All diluted samples, unknowns and standards, were run under the same qPCR conditions specified above using the GAPDH primer set. PCR efficiency for GAPDH target is $\Delta C_t \times 100\%$. In theory, the ΔCt value between samples with a 2× concentration difference should be 1 if the qPCR efficiency is 100%. Thus, if the $\Delta C_t$ is less than 1, this indicates some PCR inhibition. The results of the study are summarized below in Table 1, which shows the average $\Delta C_t$ values for the DNA samples isolated by the three different technologies (wherein Un=undiluted sample, 2×=2-fold dilution, 4×=4-fold dilution and 8×=8-fold dilution): ignore shading.

TABLE 1

| | Mag. Beads | | | | DNA Prec. | | | | IMCStip | | | |
|---|---|---|---|---|---|---|---|---|---|---|---|---|
| | Un. | 2× | 4× | 8× | Un. | 2× | 4× | 8× | Un. | 2× | 4× | 8× |
| | 22.70 | 23.69 | 24.82 | 25.69 | 22.79 | 23.65 | 25.36 | 25.88 | 22.62 | 23.72 | 24.74 | 25.62 |
| | 22.39 | 23.40 | 24.36 | 25.57 | 22.84 | 23.79 | 24.60 | 25.69 | 22.71 | 23.74 | 24.73 | 25.98 |
| | 22.50 | 23.53 | 24.82 | 25.65 | 22.70 | 23.69 | 24.50 | 25.55 | 23.07 | 23.90 | 24.95 | 25.74 |
| average $\Delta C_t$ | 1.03 ± 0.06 | | | | 0.90 ± 0.18 | | | | 0.99 ± 0.02 | | | |

Thus, in this study, it was determined that all samples produced using the kits were free of any significant amounts of PCR inhibitors that might result in false-positives in downstream applications.

DNA Fragmentation Between Kits

DNA fragmentation is common when isolating DNA from human samples. This is due to the nature of the purification process of the samples. Most protocols that are used for the isolation of DNA include vortexing, centrifugation, and vigorous mixing by pipetting. All of these actions combined can fragment the DNA. In this study, a comparison of the kits' ability to produce intact DNA was done using a qPCR assay with two sets of PCR primers, ALU 115 and ALU 247. The ALU 115 primer set amplifies both the shorter, or fragmented, and longer DNA, and the ALU 247 amplifies only the longer, or intact, DNA. The ratio between the cycle threshold ($C_t$) values given from the two primer sets for the same sample thus gives an indication of the amount of intact gDNA versus fragmented gDNA.

The following forward and reverse ALU 115 PCR oligonucleotide primers, which produce a 115 bp amplicon, were used:

```
ALU115 Repeat Forward:
                                  (SEQ ID NO: 3)
5'- CCTGAGGTCAGGAGTTCGAG -3'

ALU115 Repeat Reverse:
                                  (SEQ ID NO: 4)
5'- CCCGAGTAGCTGGGATTACA -3'
```

The following forward and reverse ALU 247 PCR oligonucleotide primers, which produce a 247 bp amplicon, were used:

```
ALU247 Repeat Forward:
                                  (SEQ ID NO: 5)
5'- GTGGCTCACGCCTGTAATC -3'

ALU247 Repeat Reverse:
                                  (SEQ ID NO: 6)
5'- CAGGCTGGAGTGCAGTGG -3'
```

For the qPCR reactions, a master-mix of 2×SYBR Green (10 μL), 2 μM forward/reverse ALU 115 primers or 2 μM forward/reverse ALU247 primers (2 μL), and water (6 μL)

with 2 μL of gDNA sample (~1 ng/μL) was used. All nine samples were run in triplicate for the qPCR assay along with a 5 ng/μL gDNA standard (Promega) in triplicate for both the ALU115 and ALU247. The cycling conditions were: 95° C. 10 minutes, then 40 cycles of 95° C. for 15 seconds, 60° C. for 30 seconds and 72° C. for 30 seconds. A melt curve, obtained by ramping from 72° C. to 95° C. at 0.3° C. per second, indicated all PCR runs were amplifying a single target.

The ratio of the two $C_t$ values (ALU 115/ALU247) were compared between kits to determine if they were numerically similar. If they were similar it was determined there was no difference in fragmentation between the kits. The ratio was also compared to the standard gDNA (Promega, PR-G1471) to compare the amount of fragmentation between the kits and the commercially available purified gDNA which was done to establish a baseline difference. The gDNA standard gave an ALU115/ALU247 ratio of 1.21±0.01. The results from each kit are shown below in Table 2, which shows a comparison of the calculated ALU 247 $C_t$/ALU 115 $C_t$ ratios for all isolated DNA samples produced in this study:

TABLE 2

|  | Mag. Beads | | DNA Prec. | | IMCStip | |
| --- | --- | --- | --- | --- | --- | --- |
|  | ALU 115 | ALU 247 | ALU 115 | ALU 247 | ALU 115 | ALU 247 |
| Sample 1 | 12.26 | 16.00 | 12.10 | 16.36 | 12.15 | 16.12 |
| Sample 2 | 12.73 | 16.98 | 11.95 | 16.16 | 12.37 | 16.58 |
| Sample 3 | 13.01 | 17.38 | 11.93 | 16.18 | 13.13 | 17.27 |
| $C_t$ Ratio | 1.324 ± 0.014 | | 1.353 ± 0.002 | | 1.327 ± 0.01 | |

In summary, all three DNA isolation technologies tested produced comparable yields of total and genomic DNA and produced PCR ready products free of PCR inhibitors with some amount of fragmentation. Given the comparability of all three technologies, the dispersive SPE pipette system of the invention offers advantages that the other two systems do not, including the ability to be fully automated without introducing centrifugation steps or the use of a magnetic manifold. Furthermore, the processing speed using the dispersive SPE pipette system per batch run is estimated at 15 minutes versus the magnetic manifold running at 25 minutes. Moreover, vacuum manifolds or centrifugation based isolation methods require much greater hands-on time. Thus, the dispersive SPE pipette system described herein is an effective DNA isolation system that offers improvements and advantages over other systems available in the art.

Example 2: Binding Capacity of Dispersive SPE Pipette System

Figure 5:
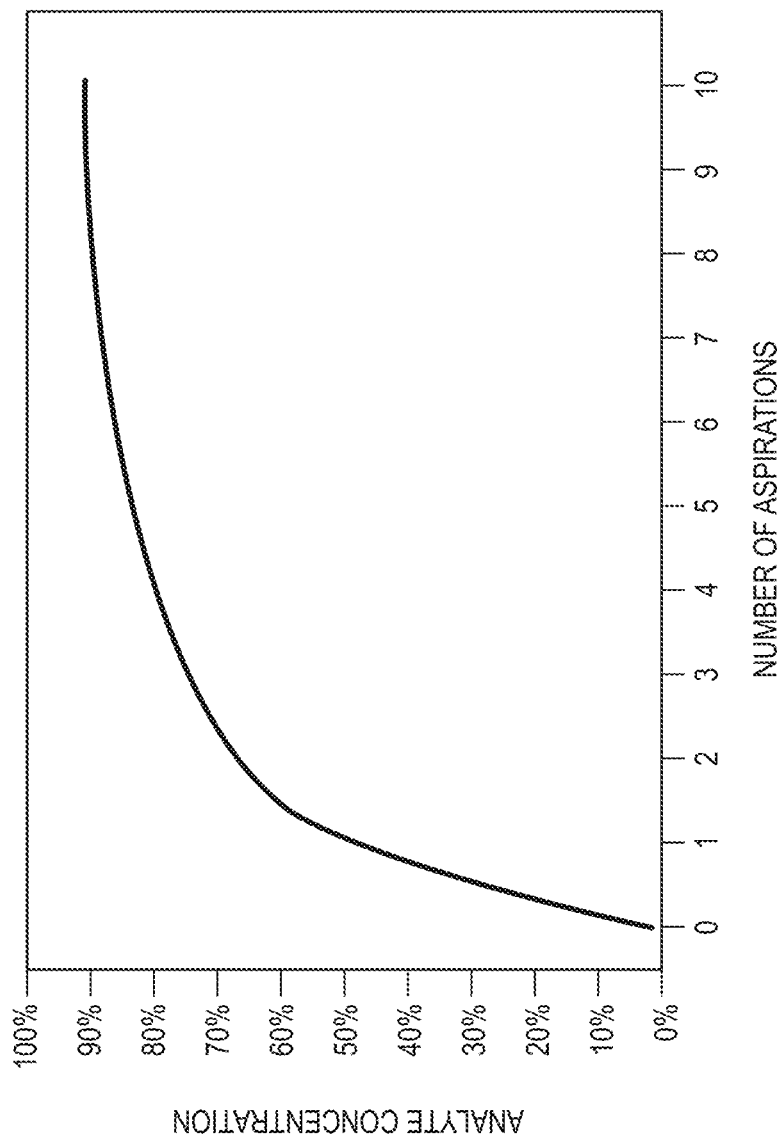
FIG. 5 is a graph showing the % concentration of analyte binding as a function of the number of aspirations into the dispersive SPE pipette system.

In this example, a series of samples were tested using the dispersive SPE pipette system of the invention to determine the binding capacity of the system as function of the number of aspirations performed. Analyte binding per aspiration was assessed using bromophenol blue dye diluted in water. The results are shown in FIG. 5, which demonstrates that the % analyte concentration bound to the resin in the pipette tip increases as a function of the number of aspirations, with at least 3 aspirations producing more binding than only 1 or 2 aspirations, and with 5 or more aspirations (e.g., 5-10) producing the highest % analyte binding. Further studies demonstrated that the binding capacity of the pipette system is limited by the concentration as well as the chemical property of the analyte of interest (i.e., log P values). Thus, the results described herein demonstrated the advantageous benefit of performing three or more aspirations per sample.

Example 3: High Throughput Enrichment of Depleted Serum Proteins Using Reverse Phase C4 Dispersive SPE Pipette System on an Automated Platform In this example, a reverse phase dispersive SPE pipette tip system (IMCStips™) was used to enrich and desalt serum samples that had undergone prior depletion treatment for removal of abundant serum proteins (referred to herein as "depleted serum"). The benefits of the method described herein include: use of a loose dispersive resin such that there is maximum contact between the resin and the analyte(s); easy integration with automated platforms; no additional equipment needed; high reproducibility; and reduced sample preparation time.

Sample Treatment

The starting sample for these extractions was pooled human serum or human serum from a healthy donor. The serum was stored at −80° C. and thawed before use. The serum was filtered using a 0.22 um filter. HiTrap™ Albumin/IgG Depletion column (GE Healthcare) was used for an initial depletion of albumin and IgG following the manufacturer's instructions. This depletion was followed by an IgY14 depletion using Sigma's spin column kit following the manufacturer's instructions. The resulting sample was then enriched using the 1 mL C4 IMCStips™ (Integrated Micro-Chromatography Systems, LLC) on the Nimbus96 automated liquid handler (Hamilton Company), as described in detail below.

Solid Phase Extraction Method

Figure 6:
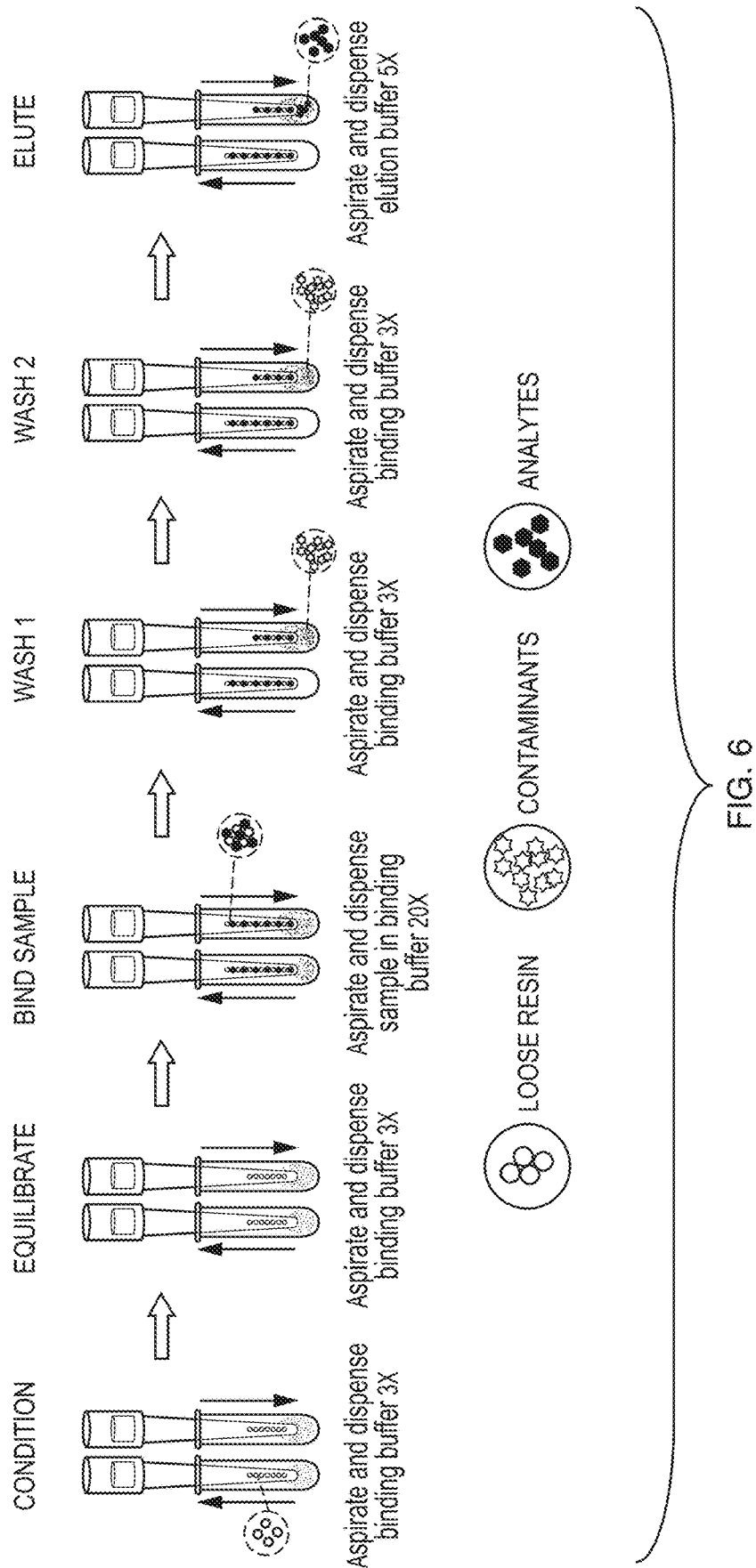
FIG. 6 is a schematic diagram of the protocol steps for use of dispersive solid phase extraction for enrichment of biomolecules (analytes) from a starting mixture (e.g., depleted serum).

All extractions used a pooled depleted serum sample as the starting material. The starting material was aliquoted to 50 μg of depleted serum protein in a 96-well plate. For the enrichment of the depleted whole protein serum sample, the 1 mL size C4 IMCStips™ containing 10 mg of reverse phase C4 dispersive resin was used following the protocol illustrated schematically in FIG. 6. The extractions were done in a 96-well format on an automated liquid handling platform.

The resin in the tip was first conditioned with 100% MeOH. This was followed by a second conditioning step by aspirating and dispensing a basic solution of 5% ammonium hydroxide three times. The sample solution was then aspirated and dispensed ten times. The resin was washed with 0.1% FA in water followed by a second wash using 0.1% FA in water. The protein was eluted with 1:1:1 mixture of isopropanol/methanol/acetone. The elution from each sample was dried down at 40-60° C. under nitrogen gas for 30 minutes. The sample was reconstituted with 50 or 100 μL of water or ammonium bicarbonate for downstream applications.

Automated SPE on Liquid Handling Platform

An automated workstation liquid handling system (e.g., Nimbus96, Hamilton Company) was used to perform the extraction. The 96-channel multi-pipetting head allows the processing of 96 samples in a single run. The automation provides greater reproducibility in comparison to a manual extraction process, as well as less physical strain on a person from repeated pipetting. The ability to develop specific liquid classes allows for the setting of aspiration speeds, hold times, blow out volumes, and mixing speeds for each liquid being aspirated which gives the end user complete control over the extraction process.

Non-limiting representative conditions for automated extraction workflow parameters are shown below in Table 3:

TABLE 3

Representative extraction workflow parameters including each liquid class used for each step in the protocol.

| Step | Buffer Composition | Aspiration Volume (µL) | Aspiration Speed (µL/sec) | Dispense Speed (µL/sec) | Settling Time (sec) | Blow Out Volume (µL) |
|---|---|---|---|---|---|---|
| First condition | 100% MeOH | 500 | 250 | 150 | 4 | 400 |
| Second condition | 1M NaOH | 400 | 20 | 20 | 10 | 300 |
| Sample | Tris HCl, NaCl | 450 | 20 | 20 | 15 | 300 |
| First Wash | H$_2$O/0.1% FA | 450 | 20 | 20 | 10 | 300 |
| Second Wash | H$_2$O/0.1% FA | 450 | 20 | 20 | 10 | 300 |
| Elution | 1:1:1 IPA/MeOH/Acetone | 500 | 20 | 25 | 25 | 300 |

Protein Assays

Total protein in each sample was quantified using a Bradford assay using bovine serum albumin as the calibration standard. The samples were then run on an SDS-Page and stained with Coomassie blue for gel imaging to compare all six samples.

Results

Figure 7:
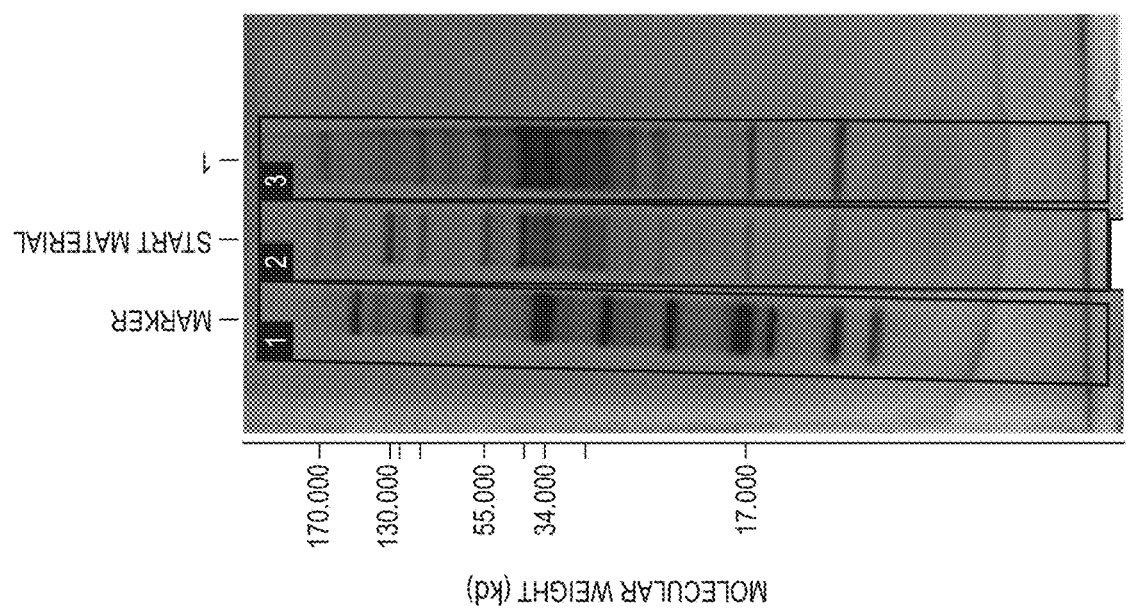
FIG. 7 is a photograph of a Coomassie blue stained SDS-PAGE gel of molecular weight ladder (lane 1), starting material of depleted serum sample (lane 2), and final sample after desalting and enrichment with 1 mL C4 dispersive SPE pipette system (lane 3).

Enrichment and desalting of serum proteins after the depletion of high abundance proteins is a critical step in the sample preparation portion of top-down and bottom up proteomics. It is vitally important that this process be carried out without compromising the integrity of the sample. In order to show the ability of the C4 dispersive SPE pipette system to reliably enrich and desalt depleted serum, an experiment was done using a sample that had been depleted and enriched according to the above protocol with the eluted proteins analyzed by SDS-PAGE. The results, shown in FIG. 7, demonstrate enrichment of serum proteins by the extraction protocol.

In follow-up experiments, several enrichments were performed to determine the reproducibility of the extraction. Inter- and intra-assay variability was 8% and 3%, respectively. Each starting protein sample contained 50 jpg of serum protein. The total protein recovery and percent recovery for each of the six samples is summarized below in Table 4:

TABLE 4

Total protein recovery of the depleted serum proteins from the starting sample

| Sample | Total Protein (µg) | % Recovery |
|---|---|---|
| 1 | 45.3 | 91 |
| 2 | 45.4 | 91 |
| 3 | 49.4 | 99 |
| 4 | 47.9 | 96 |
| 5 | 49.1 | 98 |
| 6 | 47.1 | 94 |
| Average | 47.4 ± 1.8 | 95 ± 3% |

Figure 8:
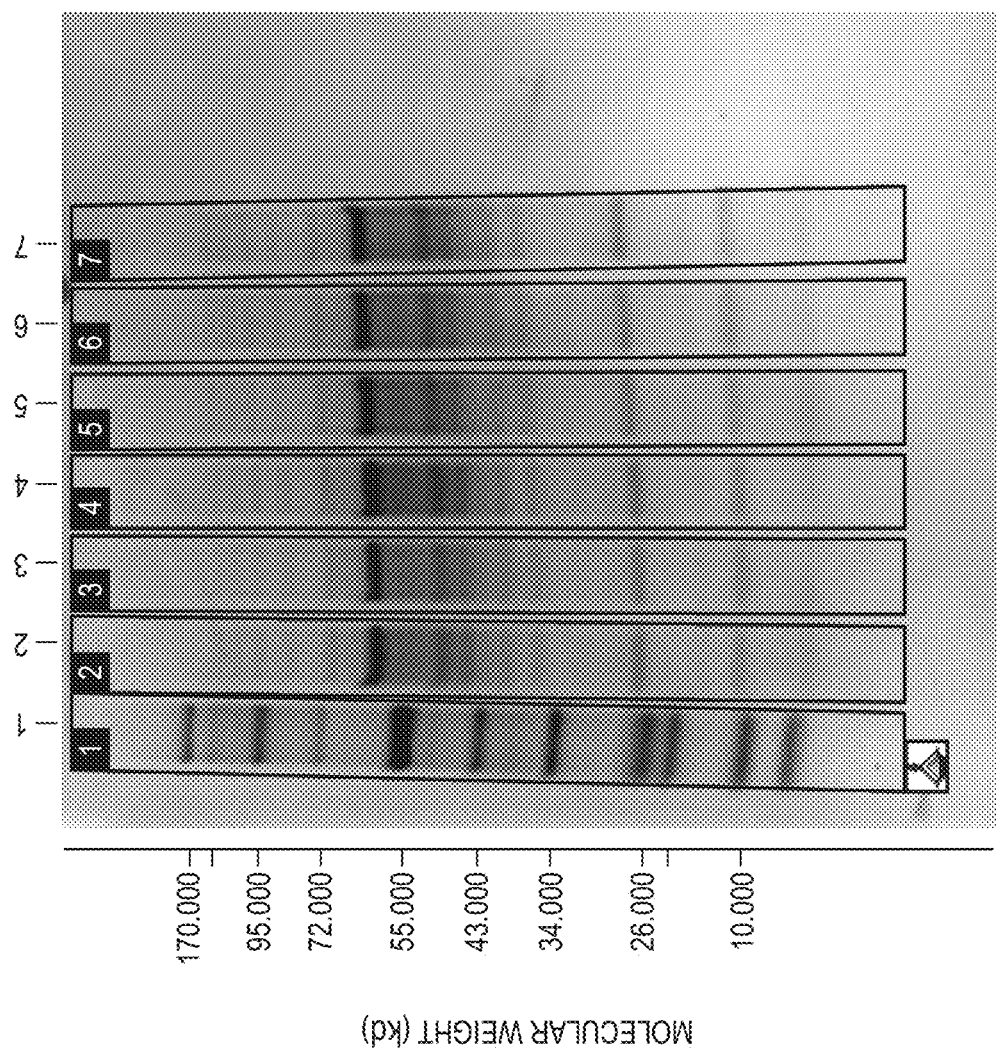
FIG. 8 is a photograph of a Coomassie blue stained SDS-PAGE gel of six depleted serum samples enriched using 1 mL C4 dispersive SPE pipette system.

All six samples were loaded on 4-20% acrylamide gel and stained with Coomassie blue. The results are shown in FIG. 8. Based on the Bradford assay and the gel image, IMC-Stips™ reliably enriched all six depleted serum samples.

The results described herein demonstrate that the dispersive SPE pipette system is suitable and beneficial for use in the field of proteomics in providing a high-throughput platform for sample preparation of biological samples for the detection of protein biomarkers in serum that would have otherwise been below the limit of detection.

Example 4: Insulin-Like Growth Factor 1 (IGF-1) Enrichment Using Reverse Phase Resin in Dispersive SPE Pipette System Insulin-like growth factor 1 (IGF-1) is a polypeptide hormone that plays an import role in childhood growth and continues to have anabolic effects in adults. IGF-1 is associated with several key regulatory pathways in the human body. It is primarily monitored as a key growth factor at young age for dwarfism (if present in small quantities) or acromegaly (if present in large quantities). More recent studies have shown the abuse of IGF-1 or its synthetic variants by athletes. Studies have also correlated abnormal IGF-1 signaling to numerous cancers and increased levels of IGF-1 in serum have been observed in lung, colon, prostate and breast cancers. Accordingly, the ability to detect IGF-1 in a biological sample, e.g., a serum sample, is desirable for a variety of clinical purposes.

Current methods utilize immunoassay-based testing to determine IGF-1 levels in serum. However, these methods have been reported to show poor correlation across different laboratories (Cox, H. D. et al. (2014) *Clinical Chemistry* 60:541-548). Alternatively, using liquid chromatography tandem mass spectrometry (LC-MS/MS) to determine IGF-1 concentration levels in human serum has been demonstrated to show better agreement between multiple laboratories (Cox et al., ibid). Accurate and robust quantification of IGF-1 from serum using mass spectrometry (MS), however, is challenging due to serum's high complexity and dynamic range. In order to analyze the serum samples by LC-MS/IS, several publications have utilized various sample preparation methods (Cox et al, ibid., Kay, R. et al. (2013) *Clin. Endocrinology* 78:424-430; Cox, H. D. and Eichner, D. (2013) *Rapid Commun. Mass Spectromr.* 27:2170-2178). These reports utilized protein precipitation approaches which use centrifugation steps or conventional solid phase extraction (SPE) tools to separate out IGF-1 from serum. These methods are limited to processing singly or at most 24 samples at a time when performed by hand, or require vacuum manifolds to exert negative pressure for 96-well SPE plates. These processes are not conducive for high throughput robotic processing, whereas the dispersive SPE pipette system described herein allows for multiple sample processing on a robotic liquid handling system with minimal hands on time.

Thus, a low cost, high throughput enrichment method for such low abundant proteins (like IGF-1) from the serum is needed to enrich target proteins prior to MS analysis. This example describes a high-throughput IGF-1 detection method using a reverse phase dispersive SPE pipette system on a robotic liquid handling system. For IGF-1, total hands-on time was 20 minutes, whereas the conventional approaches without dispersive tip extraction required at least 2 hours of hands-on time when using centrifugation methods. Other automated tip-based methods utilized fixed bed resin, which required at least 100 aspiration—dispense cycles to enrich for the target analyte, which adds at least 2 hours to complete the extraction process.

The entire workflow with the dispersive pipette technology, from start to finish was achieved on a robotic liquid handling system within 20 minutes.

Sample Preparation for Dispersive SPE Pipette System

Serum samples were prepared by diluting 20 µL of serum in 500 µL of one of three different binding buffers tested to achieve a final pH of 3, 8 or 11. Binding Buffer A was 10% acetonitrile (ACN), 2% acetic acid (pH 3). Binding Buffer B was 10% ACN, 100 mM ammonium bicarbonate (pH 8). Binding Buffer C was 10% ACN, 100 mM ammonium bicarbonate, 1% ammonium hydroxide (pH 11). The serum samples were then immediately processed using a reverse phase dispersive SPE pipette system (IMCStips™) containing 20 mg of polystyrene resin crosslinked with divinylbenzene (DVB).

Solid Phase Extraction Method

The SPE tips were first conditioned by aspirating and dispensing 600 µL of 100% acetonitrile three times. The tips were then equilibrated by aspirating 600 µL of water/0.1% formic acid three times. The serum samples were bound to the tips by aspirating 200 µL of sample in binding buffer (A, B or C) twenty times. The tips were then washed twice by aspirating 700 µL of binding buffer (A, B or C) three times. Finally, the samples were eluted by aspirating and dispensing 300 µL of acidified methanol solution five times. Alternatively, samples were eluted with 70% ACN, 100 mM ammonium bicarbonate buffer.

Following elution, samples were prepared for LC-MS/IS by drying under nitrogen flow for 20 minutes. Dried samples were then reconstituted with 10 mM dithiothreitol (DTT) for reducing the disulfide bonds at 65° C. for 30 min. Then 25 mM iodoacetamide was added for alkylation in the dark for 30 min, followed by 2 µg trypsin addition for enzymatic digestion at 37° C. for overnight.

For comparison purposes, a protein precipitation approach described in the art was also used for purification of IGF-1 from serum samples. For the protein precipitation approach, the serum sample was mixed with acidified ethanol to precipitate the proteins from serum solution. The supernatant was transferred to a new vial and then dried down. Following precipitation, the samples were treated using the same procedure described above (disulfide bond reduction, alkylation, trypsin digestion) to prepare the sample for LC-MS/MS.

To measure enriched IGF-1, ultra performance liquid chromatography (Vanquish) coupled to a TSQ-Endura triple quadrupole mass spectrometer was performed. Briefly, digested peptides were separated on a C18 column (ThermoFisher, Syncronis, 100×2.1 mm, 5 µm) using 5%-60% acetonitrile, 0.1% formic acid gradient for 10 min and 1154.04 m/z (T1), 556.6 m/z (T2), 776.85 m/z (T4) precursor ions were selected for fragments of quantification. The area under the curve (AUC) of enriched samples were compared with 10 ng IGF-1 protein digests.

Results and Discussion

Figure 9:
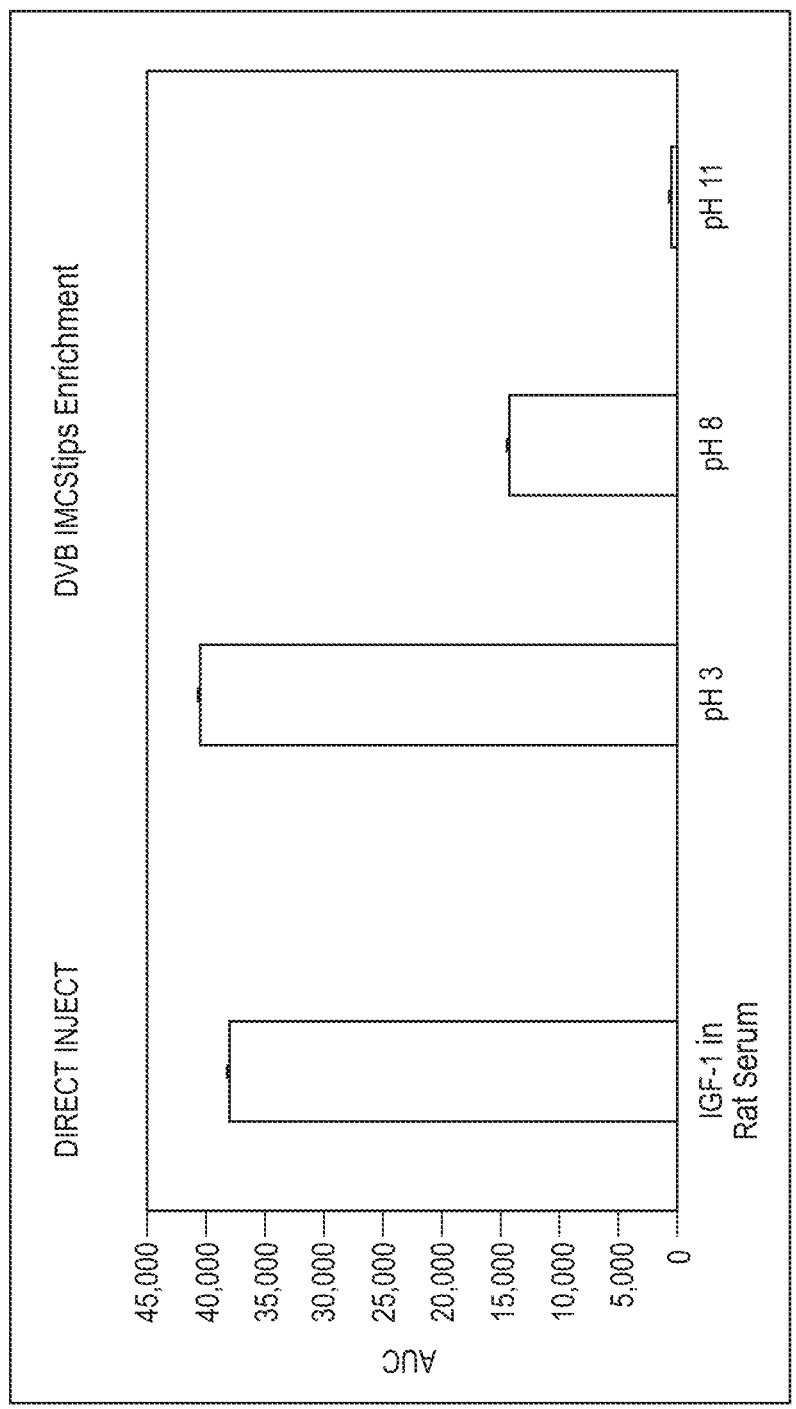
FIG. 9 is a graph plotting the recovery of human IGF-1 from rat serum from samples processed using a method known in the art ("Direct Inject") versus samples processed using a DVB dispersive SPE pipette system under three different pH conditions ("DVB IMCStips Enrichment"). Area under the curve (AUC) of 100 ng IGF-1 standard in 100 μg serum protein mixture was compared with three binding buffers.
Figure 10:
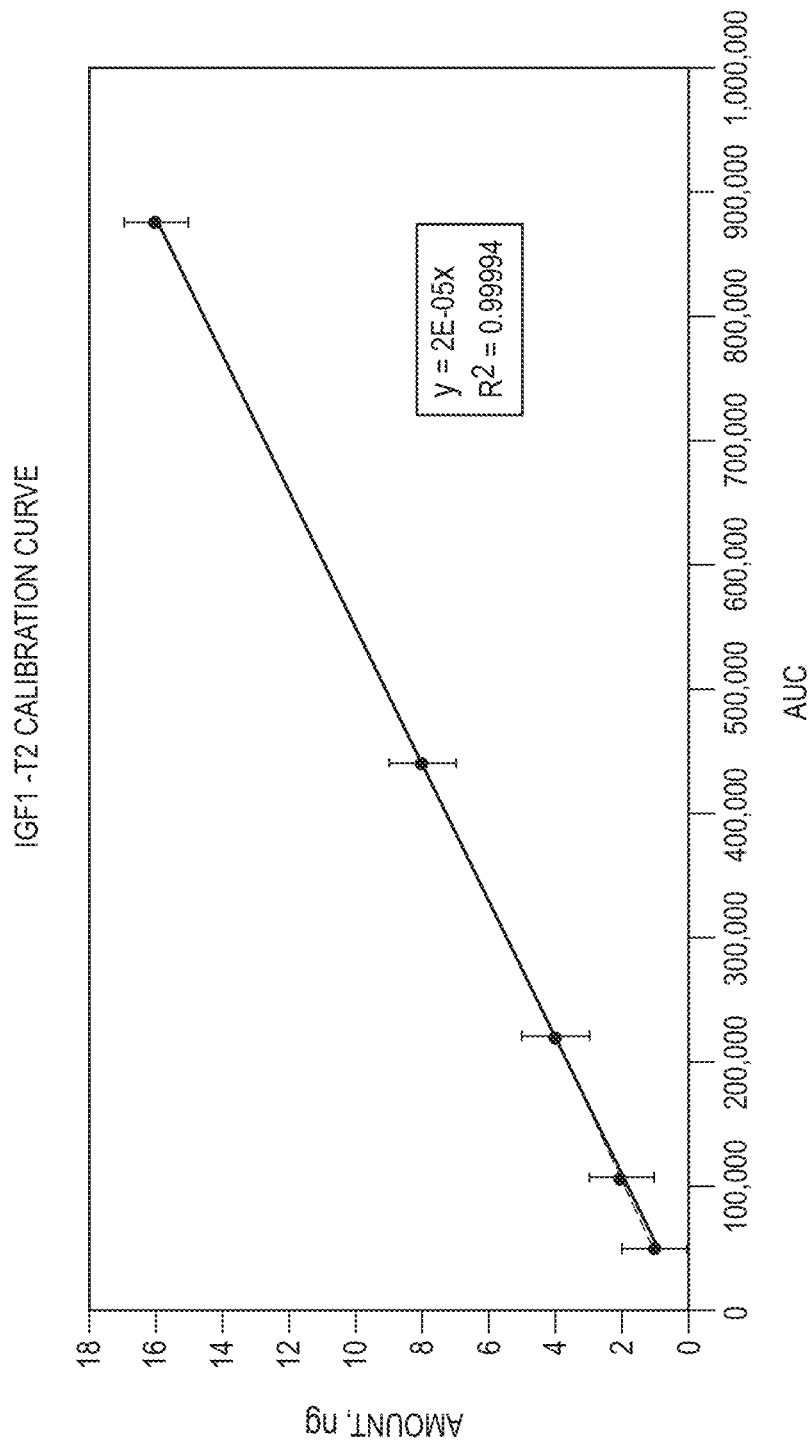
FIG. 10 is a calibration graph plotting the recovery of human IGF-1 from rat serum. The calibration standards were prepared by spiking in purified human IGF-1 (1-16 ng/mL) in 20 μL of rat serum and measured by UPLC-MS/MS.

The dispersive SPE pipette system conditions were tested against the literature reported method (protein precipitation) under three different buffer conditions (pH 3, pH 8 and pH 11). The purification results are shown in FIG. 9. The calibration standards were prepared by spiking purified human IGF-1 (1-16 ng/mL) in 20 µL of rat serum and measured by UPLC-MS/MS as shown in FIG. 10. The results showed that acidified buffer with pH of 3 showed the highest recovery among the three different pH conditions. The recovery using the dispersive SPE pipette tip system under acidic conditions led to levels of IGF-1 recovery comparable to the literature-reported protein precipitation approach. However, the dispersive SPE pipette tip system is advantageous over the protein precipitation approach in that it requires much less time and is automatable.

Example 5: Affinity Purification of Proteins Using IMAC Resin in Dispersive SPE Pipette System In this example, the dispersive SPE pipette system containing an Immobilized Metal Affinity Chromatography (IMAC) resin was used to purify a His-tagged protein from bacterial lysates.

Affinity-based extractions in complex matrices are typically time-consuming due to the labor-intensive work of hands-on pipetting and centrifugation. A typical spin column affinity extraction takes an hour to bind the sample and requires excess buffer solutions to wash off non-specific binding proteins using multiple centrifugation steps. Thus, a quick, high throughput affinity-based enrichment method for target proteins is desired to allow for quicker screening of samples. In this example, a high-throughput sample preparation method using His-tag-based protein enrichment on a robotic liquid handling system with dispersive SPE pipette extraction is described.

IMAC Dispersive SPE Pipette System

Bacterial cells containing a His-tagged protein were lysed with a commercial reagent (B-PER) to prepare a bacterial lysate for applying to the pipette system to purify the His-tagged protein.

A Cobalt-IMAC dispersive SPE pipette system (prepared from a 50% Cobalt-IMAC slurry) was conditioned by aspirating 250 µL of Binding Buffer (20 mM sodium phosphate, 0.5 M NaCl, 20-40 mM imidazole, pH 7.4) three times. The tips were then equilibrated by aspirating 250 µL of Binding Buffer three times. The sample was bound to the tips by aspirating 200 µL of sample in Binding Buffer twenty times. The tips were washed twice by aspirating 250 µL of Binding Buffer three times. Finally, the bound protein was eluted by aspirating 100 µL of Elution Buffer (20 mM sodium phosphate, 0.5 M NaCl, 500 mM imidazole, pH 7.4) five times.

Results and Discussion

Figure 11B:
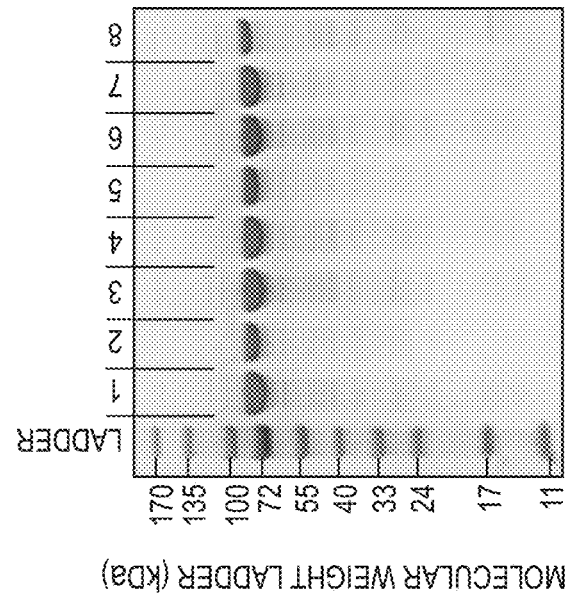
FIGS. 11A-B are photographs of Coomassie blue stained SDS-PAGE gels.
Figure 11A:
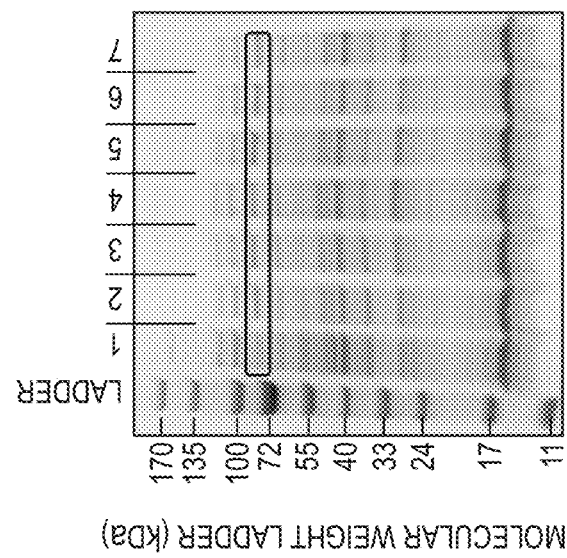

As a control, approximately 1 OD of transformed bacterial cells were lysed with B-PER and 10 µL of the lysate was mixed with loading dye. The entire sample solution was then run on SDS-PAGE to visualize total protein content of the induced cells. The results are shown in FIG. 11A, with the His-tagged protein indicated by the boxed region. For visualization of the dispersive SPE pipette tip proteins, the affinity-enriched proteins were further concentrated using a 30 KDa molecular weight cutoff centrifuge filtration unit and loaded on SDS-PAGE. The results are shown in FIG. 11B. The results demonstrate that the IMAC dispersive SPE pipette system is effective in purifying a His-tagged protein from a biological sample (crude bacterial lysate).

Example 6: Affinity Purification of Immunoglobulin Using Protein A Resin in Dispersive SPE Pipette System In this example, the dispersive SPE pipette system containing a Protein A resin was used to purify a immunoglobulin from serum samples.

Affinity-based extractions in complex matrices are typically time-consuming due to the labor-intensive work of hands-on pipetting and centrifugation. A typical spin column affinity extraction takes an hour to bind the sample and requires excess buffer solutions to wash off non-specific binding proteins using multiple centrifugation steps. Thus, a quick, high throughput affinity-based enrichment method for target proteins is desired to allow for quicker screening of samples. In this example, a high-throughput sample preparation method using Protein A-based immunoglobulin enrichment on a robotic liquid handling system with dispersive SPE pipette extraction is described.

Protein A Dispersive SPE Pipette System

Standard serum samples were used as the source from which immunoglobulin was purified.

A Protein A dispersive SPE pipette system (prepared from a 50% MabSelect SuRe™ LX slurry; GE Lifesciences) was conditioned by aspirating 250 µL of Binding Buffer (20 mM sodium phosphate, 0.15 M sodium chloride) three times. The tips were then equilibrated by aspirating 250 µL of Binding Buffer three times. Serum sample was bound to the tips by aspirating 200 µL of sample in Binding Buffer twenty times. The tips were washed twice by aspirating 250 µL of Binding Buffer three times. Finally, the bound immunoglobulin was eluted by aspirating 100 µL of Elution Buffer (0.1 M sodium citrate, pH 3.5) five times. Samples were then neutralized with neutralization buffer (1 M Tris, pH 9.0).

For comparison purposes, serum samples also were processed for immunoglobulin purification by batch extraction using a standard spin column format with the same resin type and same resin amounts. The spin columns were washed and equilibrated three times with Binding Buffer, with centrifugation to remove the wash solution and equilibration solutions after each buffer addition. Samples were bound by adding diluted serum and binding buffer solution, followed by incubation on a rocker for one hour. Spin columns were then washed by aspirating 250 µL of Binding Buffer three times. Finally, the bound immunoglobulin was eluted by aspirating 100 µL of Elution Buffer five times.

Results and Discussion

Figure 12:
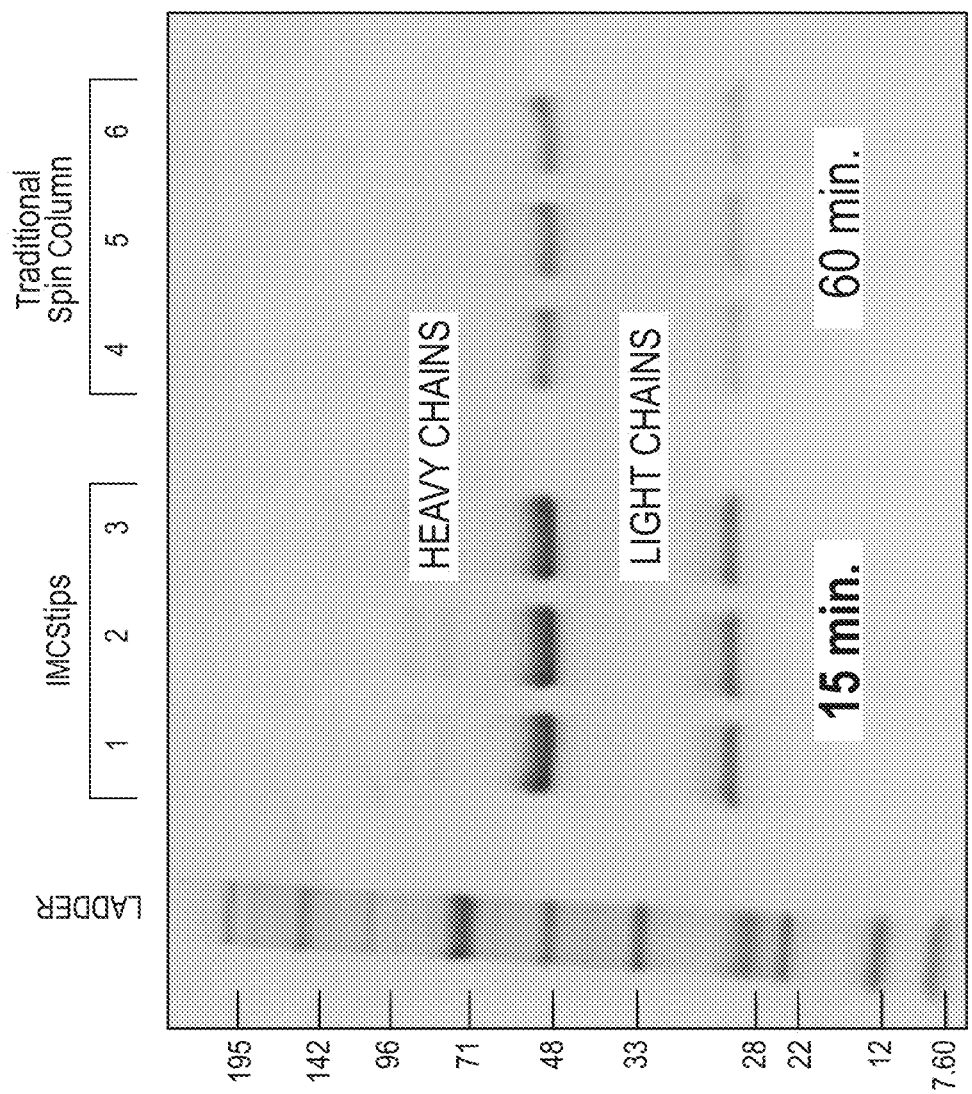
FIG. 12 is a photograph of a Coomassie blue stained SDS-PAGE gel of human immunoglobulin G purified from serum samples using Protein A dispersive SPE pipette system (IMCStips) versus traditional spin column format.

The results of the immunoglobulin purification using the dispersive SPE pipette system versus traditional spin column are shown in FIG. 12. The purification using the dispersive SPE pipette system leverages turbulent mixing to achieve rapid isolation of IgG to achieve similar or better yields than traditional spin column format as shown in FIG. 12. In particular, the Protein A dispersive SPE pipette system affinity purification approach shortened the incubation step from 60 minutes to 15 minutes without losing any recovery yield.

Example 7: Selective Enrichment of Phosphopeptides from Cell Lysates Using TiO$_2$ Dispersive SPE Pipette System In this example, a TiO$_2$ dispersive SPE pipette system was used to enrich for phosphopeptides from a complex protein digest. The TiO$_2$ dispersive SPE pipette system in combination with the optimized phosphopeptide enrichment buffers allowed for higher specificity, lower background and for direct MS analysis without the need for a post-cleanup step. The extraction followed a simple 8-step pipetting bind, wash, elute protocol that removed the need for labor-intensive centrifugation steps.

TiO$_2$ Dispersive SPE Pipette System

Tryptic digests of HEK 293 cell lysates were used as the sample material from which phosphopeptides were to be purified. Cells were lysed with 8M urea, with brief pulsating sonication, followed by trypsin digestion according to the vendor protocol. Samples were reconstituted with 200 µL of Sample Solution (25% Lactic acid, 60% ACN, 0.3% TFA), briefly vortexed and spun down.

The resin within the TiO$_2$ dispersive SPE pipette system first was activated by aspirating and dispensing Activation Solution (100% acetonitrile (ACN)). The tips were then conditioned by aspirating and dispensing Condition Solution (80%0 ACN, 0.4% trifluoroacetic acid (TFA)). The tips where then equilibrated by aspirating and dispensing Equilibration Solution (25% Lactic acid, 60% ACN, 0.3% TFA) three times. The sample was bound to the tips by aspirating 200 µL of the trypic digests in Sample Solution twenty times. The tips were then washed once by aspirating and dispensing Sample Solution three times and then washed a second time by aspirating and dispensing Condition Solution three times. Finally, the bound phosphopeptides were eluted twice (Elution 1 and Elution 2) by aspirating and dispersing Elution Solution (1.5% NH$_4$OH, 10% ACN) three times. Elution 1 and Elution 2 were combined, the sample was dried in a centrivap until all liquid was removed, and the sample was reconstituted with 20 µL Reconstitution Solution (0.1% Formic Acid). Samples were briefly vortexed and spun down, prior to MS analysis.

For comparison purposes, the identical sample amounts were processed by standard spin column using the same amount of titanium oxide resin.

Results and Discussion

Figure 13:
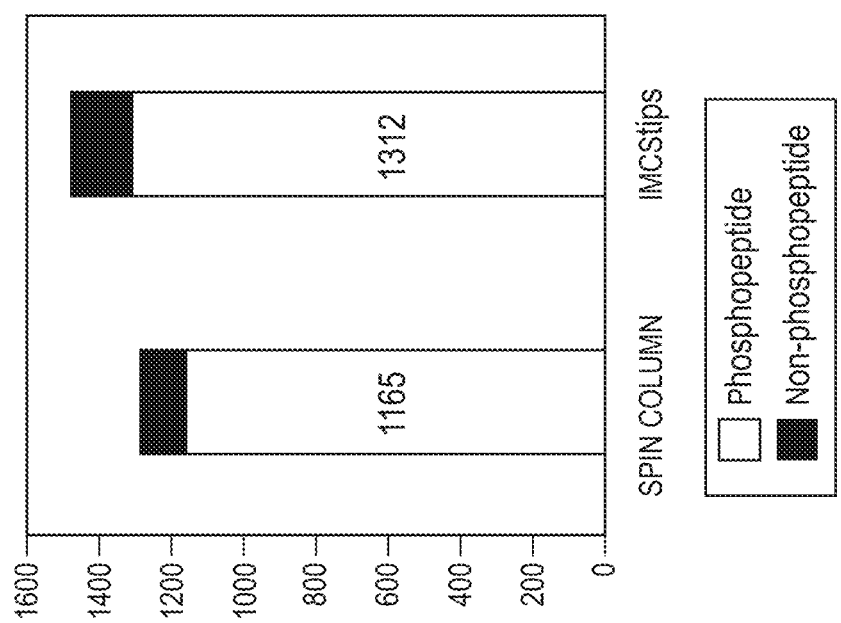
FIG. 13 is a bar graph showing recovery of phosphopeptides isolated from tryptic digests of cell lysate using traditional spin columns or using $TiO_2$ dispersive SPE pipette system (IMCStips).

The results of the phosphopeptide purification using the TiO$_2$ dispersive SPE pipette system versus standard spin columns is shown in FIG. 13. The results demonstrated that phosphopeptide enrichment using dispersive pipette extraction technology improved the overall recovery of the analytes in comparison to spin column format, with the dispersive pipette extraction approach showing a 12.6% increase in phosphopeptide recoveries. The dispersive SPE pipette technology facilitated enhanced binding of analytes of interest, while limiting non-specific binding, leading to phosphopeptide enrichment with greater than 85% specificity.

Example 8: Rapid Removal of Protein from Serum Using Reverse Phase C4 Dispersive SPE Pipette System on an Automated Platform In this example, a reverse phase dispersive SPE pipette tip system (IMCStips™) was used to remove over 99% of protein from serum while still retaining many of the smaller molecules in the flow through. The benefits of the method described herein include: use of a loose dispersive resin such that there is maximum contact between the resin and the analyte(s); easy integration with automated platforms; no additional equipment needed; high reproducibility; and reduced sample preparation time.

Sample Treatment

The starting sample for these extractions was pooled human serum. The serum was stored at −80° C. and thawed before use. The serum was unfiltered and used as provided by vendor.

Solid Phase Extraction Method

All extractions used a pooled depleted serum sample as the starting material. The extractions were done in a 96-well format on an automated liquid handling platform. The starting material was aliquoted to 100 µL of serum in a 96-well plate. 1 mL size C4 IMCStips™, containing 40 mg of reverse phase C4 dispersive resin, were used. First, the tips were conditioned with 100% isopropanol followed by equilibration with water. For the protein crash step, 100 µL of serum was aspirated into the tip followed by aspiration of 500 µL of isopropanol into the tip with the serum. The sample was then dispensed and re-aspirated into the tip. The cycle was repeated five times. The final solution that was dispensed from the tip was then dried and reconstituted in water. No detectable level of protein was measured by Bradford assay.

Automated SPE on Liquid Handling Platform

An automated workstation liquid handling system (e.g., Nimbus96, Hamilton Company) was used to perform the protein removal. The 96-channel multi-pipetting head allows the processing of 96 samples in a single run. The automation provides greater reproducibility in comparison to a manual extraction process, as well as less physical strain on a person from repeated pipetting. The ability to develop specific liquid classes allows for the setting of aspiration speeds, hold times, blow out volumes, and mixing speeds for each liquid being aspirated which gives the end user complete control over the extraction process.

Non-limiting representative conditions for automated extraction workflow parameters are shown below in Table 5:

TABLE 5

Representative extraction workflow parameters including each liquid class used for each step in the protocol.

| Step | Buffer Composition | Aspiration Volume (µL) | Aspiration Speed (µL/sec) | Dispense Speed (µL/sec) | Settling Time (sec) | Blow Out Volume (µL) |
| --- | --- | --- | --- | --- | --- | --- |
| Condition | 100% IPA | 100-1000 | 10-400 | 25-250 | 4-10 | 20-400 |
| Equilibrate | Water | 100-1000 | 10-400 | 25-250 | 4-10 | 20-400 |
| Sample | Serum | 100-1000 | 10-400 | 25-250 | 4-10 | 20-400 |
| Follow | 100% IPA | 100-1000 | 10-400 | 25-250 | 4-10 | 20-400 |

Protein Assays

Total protein in each sample was quantified using a Bradford assay using bovine serum albumin as the calibration standard.

Liquid Chromatography Quadropole Orbitrap Mass Spectrometry

A total of six samples were analyzed by Q Exactive HF (Thermo Scientific). One sample was to establish a blank solvent baseline for centrifugation method by using 100 µL of water with 500 µL of methanol in the same plastic microfuge container as the other samples. Samples for the centrifugation method were prepared by precipitating 100 µL of serum with 500 µL of methanol. A baseline sample was prepared for IMCStips™ by aspirating 100 µL of water followed by 500 µL of isopropanol in the same plastic microfuge container as the other samples. Samples for IMCStips™ method were prepared by precipitating 100 µL of serum with 500 µL of isopropanol inside the tips.

Two different columns were used to monitor in both positive and negative ion modes. Reverse phase chromatography was performed using C18

Results

Effective depletion of proteins is a critical step in the sample preparation portion of metabolomics. Typically, the process is performed using centrifugation where the serum sample is mixed with an organic solution such as methanol, isopropanol, acetone or other similar solvents. It is vitally important that this process is carried out without compromising the integrity of the sample. In order to show the ability of the dispersive SPE pipette system to reliably remove proteins, an experiment was done using human serum samples, which contain a protein concentration ranging 60-80 mg/mL. The flow through solution, the solution comprised of the serum with isopropanol after passing through the tips with C4 resin, was dried and reconstituted with 5% methanol in water. Bradford assay was used to determine that there were no detectable levels of protein in the reconstituted solution.

Figure 14:
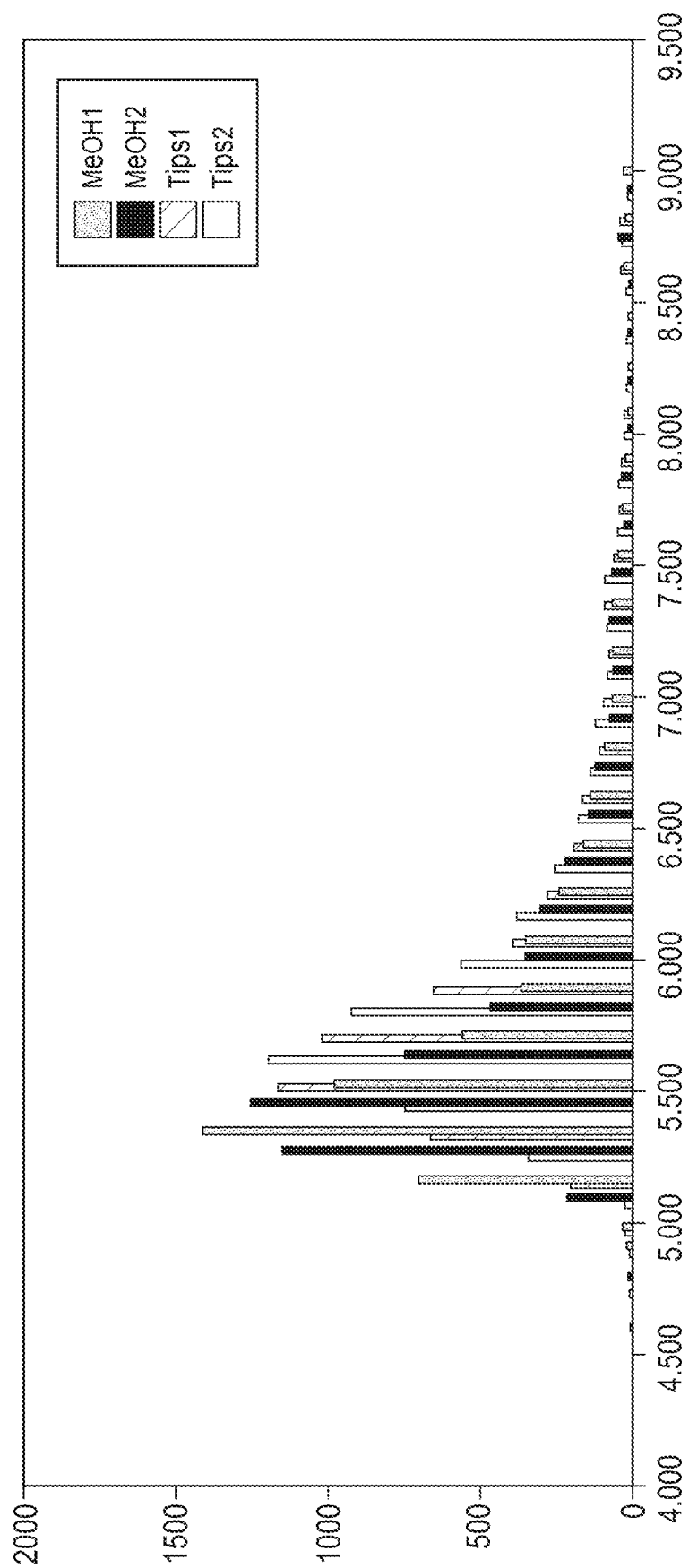
FIG. 14 is a graph showing results of liquid chromatography orbitrap mass spectrometry analysis of samples processed using traditional centrifugation methods (MeOH1 and MeOH2) versus C4 dispersive SPE pipette system (Tips1 and Tips2).

In follow-up experiments, duplicate samples that were processed with the C4 resin dispersive SPE pipette system and traditional centrifugation method were analyzed by liquid chromatography orbitrap mass spectrometry for detection of various small molecules. The results, shown in FIG. 14, demonstrate similar signal intensities for the small molecules on the mass spectrometer with minimal effects from proteins.

Thus, these results demonstrate that the reverse phase C4 resin dispersive SPE pipette system is effective in rapidly removing proteins from serum samples in an automated format.

EQUIVALENTS

Those skilled in the art will recognize, or be able to ascertain using no more than routine experimentation, many equivalents of the specific embodiments of the invention described herein. Such equivalents are intended to be encompassed by the following claims.

| SUMMARY OF SEQUENCE LISTING | |
| --- | --- |
| SEQ ID NO: | DESCRIPTION |
| 1 | CTCTGCTCCTCCTGTTCGAC |
| 2 | TTCCCGTTCTCAGCCTTGAC |
| 3 | CCTGAGGTCAGGAGTTCGAG |
| 4 | CCCGAGTAGCTGGGATTACA |
| 5 | GTGGCTCACGCCTGTAATC |
| 6 | CAGGCTGGAGTGCAGTGG |

The invention claimed is:

1. A pipette tip for solid phase extraction comprising:
a housing having a proximal end with a lower opening adapted for passage of a liquid and a distal end with an upper opening dimensioned to fit on the end of a dispenser;
a first frit inside the housing above the lower opening, the first frit: (i) being made of a material that does not bind a biomolecule of interest; and (ii) having an average porosity measured in microns;
a second frit inside the housing and positioned between the first frit and the upper opening; and
a plurality of absorptive particles that bind the biomolecule of interest inside the housing and confined between the first frit and the second frit, the absorptive particles having an average diameter measured in microns,
wherein the absorptive particles and the second frit are spaced apart so as to form a void therebetween, and wherein the void is dimensioned so that the absorptive particles can travel freely within the void allowing thorough mixing between the absorptive particles and a sample solution when the sample solution is in the void; and
wherein the average porosity of the first frit is at least 10 microns larger than the average diameter of the absorptive particles.

2. The pipette tip of claim 1, wherein the housing has a proximal end with a lower opening having an inner diameter of at least 0.05 inches.

3. The pipette tip of claim 1, wherein the housing has a first inflection point and a second inflection point, the second inflection point being located closer to the lower opening than the first inflection point, and wherein a taper angle between the lower opening and the second inflection point is 5 degrees or less.

4. The pipette tip of claim 1, wherein the first frit has an average porosity of 60-80 microns and the absorptive particles have a diameter of 40-70 microns.

5. The pipette tip of claim 1, wherein the first frit has an average porosity of 70 microns.

6. The pipette tip of claim 1, wherein the first frit is a porous polymer plug.

7. The pipette tip of claim 1, wherein the first frit is a porous polymer plug with an average porosity of 60-80 microns.

8. The pipette tip of claim 7, wherein the first frit is a polyethylene plug, a polypropylene/polyethylene plug or a fluorinated polyethylene plug.

9. The pipette tip of claim 1, which further comprises a baffle system contained within the housing, wherein the baffle system is shaped to disrupt movement of the absorptive particles when the sample solution is introduced into the housing.

10. The pipette tip of claim 1, wherein the dispenser is selected from the group consisting of a pipettor, a liquid dispensing apparatus, a robotic liquid dispensing apparatus and a piston head.

11. The pipette tip of claim 1, wherein the absorptive particles comprise a material selected from the group consisting of hydroxylated materials, silica, derivatized silica, silica/glass materials, ceramic materials, modified polymeric materials, charge switchable resins, negatively charged resins, reverse phase resins, ion exchange resins and affinity resins.

12. The pipette tip of claim 11, wherein the absorptive particles comprise a reverse phase resin selected from the group consisting of divinylbenzene (DVB) resins, C4 resins, C8 resins and C18 resins.

13. The pipette tip of claim 11, wherein the absorptive particles comprise an ion exchange resin selected from the group consisting of weak anion exchange resins, weak cation exchange resins, strong anion exchange resins and strong cation exchange resins.

14. The pipette tip of claim 11, wherein the absorptive particles comprise an affinity resin selected from the group consisting of a Protein A resin, a Protein G resin, an IMAC resin, an albumin affinity resin and a titanium oxide resin.

15. The pipette tip of claim 1, wherein the biomolecule of interest is selected from the group consisting of nucleic acids, proteins, polypeptides, peptides and phosphopeptides.

16. A pipette tip for solid phase extraction comprising:
a housing having a proximal end with a lower opening having an inner diameter of at least 0.05 inches and a distal end with an upper opening dimensioned to fit on the end of a dispenser, wherein the housing has a first inflection point and a second inflection point, the second inflection point being located closer to the lower opening than the first inflection point, wherein a taper angle between the lower opening and the second inflection point is 5 degrees or less;
a first frit inside the housing above the lower opening, the first frit: (i) being made of a material that does not bind a biomolecule of interest; and (ii) having an average porosity measured in microns;
a second frit inside the housing and positioned between the first frit and the upper opening; and
a plurality of absorptive particles that bind the biomolecule of interest inside the housing and confined between the first frit and the second frit, the absorptive particles having an average diameter measured in microns, wherein the absorptive particles and the second frit are spaced apart so as to form a void therebetween, and wherein the void is dimensioned so that the absorptive particles can travel freely within the void allowing thorough mixing between the absorptive particles and a sample solution when the sample solution is in the void; and wherein the average porosity of the first frit is at least 10 microns larger than the average diameter of the absorptive particles.

* * * * *

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctctgctcct cctgttcgac                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttcccgttct cagccttgac                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cctgaggtca ggagttcgag                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cccgagtagc tgggattaca                                              20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtggctcacg cctgtaatc                                               19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caggctggag tgcagtgg                                                18

```
<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5
```